(12) United States Patent
Vase

(10) Patent No.: US 12,721,980 B2
(45) Date of Patent: Sep. 1, 2026

(54) DEVICES AND SYSTEMS FOR ACCESS AND NAVIGATION OF CEREBROSPINAL FLUID SPACE

(71) Applicant: PHARAOH NEURO, INC., Minneapolis, MN (US)

(72) Inventor: Abhi Vase, Los Altos Hills, CA (US)

(73) Assignee: PHARAOH NEURO, INC.

( * ) Notice: Subject to any disclaimer, the term of this patent is extended or adjusted under 35 U.S.C. 154(b) by 794 days.

(21) Appl. No.: 17/235,615

(22) Filed: Apr. 20, 2021

(65) Prior Publication Data

US 2021/0236782 A1 Aug. 5, 2021

Related U.S. Application Data

(63) Continuation of application No. 14/743,652, filed on Jun. 18, 2015, now abandoned.

(Continued)

(51) Int. Cl.
*A61M 25/00* (2006.01)
*A61B 17/221* (2006.01)

(Continued)

(52) U.S. Cl.
CPC ......... *A61M 27/006* (2013.01); *A61B 17/221* (2013.01); *A61M 25/0026* (2013.01);

(Continued)

(58) Field of Classification Search
CPC .. A61M 2025/0002; A61M 2025/0031; A61M 2025/0042; A61M 2025/0059; A61M 2025/0681; A61M 2025/1079; A61M 2205/3331; A61M 2210/0693; A61M 25/0026; A61M 25/003; A61M 25/0032; A61M 25/0041; A61M 25/0043; A61M 25/0045; A61M 25/0053; A61M 25/0067; A61M 25/0068; A61M 25/007;

(Continued)

(56) References Cited

U.S. PATENT DOCUMENTS 2,969,066 A 1/1961 Holter et al.
3,419,010 A 12/1968 Williamson (Continued)

FOREIGN PATENT DOCUMENTS

CA 2407214 A1 4/2003
CA 2597293 A1 8/2006

(Continued)

OTHER PUBLICATIONS

Elefteriades et al; Litigation in Nontraumatic Aortic Diseases—a Tempest in the Malpractice Maelstrom, Cardiology, vol. 109, pp. 263-272, 2008.

(Continued)

*Primary Examiner* — Kai H Weng
(74) *Attorney, Agent, or Firm* — Seager, Tufte & Wickhem LLP

(57) ABSTRACT

The present disclosure relates to accessing, removing, exchanging and recirculating cerebrospinal fluid (CSF). Devices, systems and methods disclosed herein are used to safely and efficiently navigate the space at and around the brain and spinal cord where the CSF flows through the body, also known as the CSF space.

13 Claims, 38 Drawing Sheets

Related U.S. Application Data

(60) Provisional application No. 62/038,998, filed on Aug. 19, 2014.

(51) Int. Cl.
*A61M 27/00* (2006.01)
*A61B 5/00* (2006.01)
*A61B 17/12* (2006.01)
*A61B 17/22* (2006.01)
*A61B 90/00* (2016.01)
*A61M 25/06* (2006.01)
*A61M 25/10* (2013.01)

(52) U.S. Cl.
CPC ...... *A61M 25/003* (2013.01); *A61M 25/0043* (2013.01); *A61M 25/0053* (2013.01); *A61M 25/0068* (2013.01); *A61M 25/007* (2013.01); *A61M 25/0097* (2013.01); *A61B 5/00* (2013.01); *A61B 17/12* (2013.01); *A61B 2017/22034* (2013.01); *A61B 2017/22051* (2013.01); *A61B 2017/2215* (2013.01); *A61B 2090/064* (2016.02); *A61M 2025/0002* (2013.01); *A61M 2025/0031* (2013.01); *A61M 25/0032* (2013.01); *A61M 25/0041* (2013.01); *A61M 2025/0042* (2013.01); *A61M 25/0045* (2013.01); *A61M 2025/0059* (2013.01); *A61M 25/0067* (2013.01); *A61M 2025/0681* (2013.01); *A61M 25/1011* (2013.01); *A61M 2025/1079* (2013.01); *A61M 2205/3331* (2013.01); *A61M 2210/0693* (2013.01)

(58) Field of Classification Search
CPC .......... A61M 25/0097; A61M 25/1011; A61M 27/006; A61B 17/12; A61B 17/221; A61B 2017/22034; A61B 2017/22051; A61B 2017/2215; A61B 2090/064; A61B 5/00
See application file for complete search history.

(56) References Cited

U.S. PATENT DOCUMENTS 3,867,937 A 2/1975 Schwartz
3,889,687 A 6/1975 Harris et al.
4,378,797 A 4/1983 Osterholm
4,446,154 A 5/1984 Osterholm
4,451,251 A 5/1984 Osterholm
4,551,137 A 11/1985 Osborne
4,686,085 A 8/1987 Osterholm
4,767,409 A 8/1988 Brooks
4,830,849 A 5/1989 Osterholm
4,888,115 A 12/1989 Marinaccio et al.
4,904,237 A 2/1990 Janese
4,950,232 A 8/1990 Ruzicka et al.
4,958,901 A 9/1990 Coombs
5,160,323 A 11/1992 Andrew
5,171,226 A 12/1992 McCrory
5,190,529 A 3/1993 McCrory et al.
5,334,315 A 8/1994 Matkovich et al.
5,396,899 A 3/1995 Strittmatter
5,405,316 A 4/1995 Magram
5,423,738 A 6/1995 Robinson et al.
5,462,667 A 10/1995 Wollinsky et al.
5,531,673 A 7/1996 Helenowski
5,601,727 A 2/1997 Bormann et al.
5,658,264 A * 8/1997 Samson ............. A61M 25/005 604/526
5,683,357 A 11/1997 Magram
5,755,968 A 5/1998 Stone
5,772,607 A 6/1998 Magram
5,836,928 A 11/1998 Gerber et al.
5,897,528 A 4/1999 Schultz
5,941,853 A 8/1999 Collins
5,947,689 A 9/1999 Schick
5,947,940 A * 9/1999 Beisel ................ A61M 25/005 604/526
5,948,441 A 9/1999 Lenk et al.
5,980,480 A 11/1999 Rubenstein et al.
6,013,051 A 1/2000 Nelson
6,056,725 A 5/2000 Elsberry
6,217,552 B1 4/2001 Barbut et al.
6,238,382 B1 5/2001 Schock et al.
6,264,625 B1 7/2001 Rubenstein et al.
6,326,044 B1 12/2001 Lindquist
6,379,331 B2 4/2002 Barbut et al.
6,383,159 B1 5/2002 Saul et al.
6,383,380 B1 5/2002 Kopf
6,387,290 B1 5/2002 Brody et al.
6,468,219 B1 10/2002 Njemanze
6,537,241 B1 3/2003 Odland
6,558,353 B2 5/2003 Zohmann
6,575,928 B2 6/2003 Saul et al.
6,594,880 B2 7/2003 Elsberry
6,616,651 B1 * 9/2003 Stevens ............... A61M 25/005 604/524
6,641,563 B1 11/2003 Vitullo et al.
6,682,508 B1 1/2004 Meythaler et al.
6,689,085 B1 2/2004 Rubenstein et al.
6,689,756 B2 2/2004 Hesson et al.
6,699,269 B2 3/2004 Khanna
6,709,426 B2 3/2004 Gijsbers et al.
6,758,832 B2 7/2004 Barbut et al.
6,830,561 B2 12/2004 Jansen et al.
6,849,185 B1 2/2005 Wu et al.
6,875,192 B1 4/2005 Saul et al.
6,969,383 B2 11/2005 Hildebrand
7,011,647 B2 3/2006 Purdy et al.
7,025,742 B2 4/2006 Rubenstein et al.
7,108,680 B2 9/2006 Rohr et al.
7,118,549 B2 10/2006 Chan
7,150,737 B2 12/2006 Purdy et al.
7,181,289 B2 2/2007 Pflueger et al.
7,189,221 B2 3/2007 Silverberg et al.
7,214,211 B2 5/2007 Woehr et al.
7,252,659 B2 8/2007 Shehada et al.
7,318,834 B2 1/2008 Njemanze
7,455,666 B2 11/2008 Purdy
7,708,716 B2 5/2010 Shah
7,787,954 B2 8/2010 Purdy
7,842,002 B2 11/2010 Mantle
7,850,723 B1 12/2010 Magers
7,887,503 B2 2/2011 Geiger
8,029,495 B2 10/2011 Pyles
8,131,353 B2 3/2012 Purdy
8,137,334 B2 3/2012 Heruth et al.
8,231,586 B2 7/2012 Kizer et al.
8,357,296 B2 1/2013 Bonhomme et al.
8,398,581 B2 3/2013 Panotopoulos
8,435,204 B2 5/2013 Lad et al.
8,444,661 B2 5/2013 Nair et al.
8,475,419 B2 7/2013 Eckermann
8,486,023 B2 7/2013 Pyles
8,486,104 B2 7/2013 Samson et al.
8,512,280 B2 8/2013 Rozenberg et al.
8,518,636 B2 8/2013 Bosch et al.
8,523,930 B2 9/2013 Saunders et al.
8,603,057 B2 12/2013 Hoffman et al.
8,669,044 B2 3/2014 Chiu et al.
8,679,751 B2 3/2014 Huang
8,721,642 B1 5/2014 Sullivan
8,905,968 B2 12/2014 Thomas
9,205,184 B2 12/2015 Eckermann
9,211,163 B1 12/2015 Jaramaz et al.
9,387,311 B1 7/2016 Heilman et al.
10,569,064 B2 2/2020 Vase et al.
10,632,237 B2 4/2020 Meyering et al.
10,695,545 B2 6/2020 Hedstrom et al.
10,850,235 B2 12/2020 Meyering et al.
2002/0123714 A1 9/2002 Saul et al.
2002/0156482 A1 10/2002 Scribner et al.
2002/0193285 A1 12/2002 Tesson et al.
2003/0004495 A1 1/2003 Saul

(56) References Cited

U.S. PATENT DOCUMENTS

2003/0014016 A1 1/2003 Purdy
2003/0028137 A1 2/2003 Levin
2003/0032915 A1 2/2003 Saul
2003/0065309 A1 4/2003 Barnitz
2003/0072761 A1 4/2003 Lebowitz
2003/0083698 A1 5/2003 Whitehurst et al.
2003/0097082 A1 5/2003 Purdy et al.
2003/0129134 A1 7/2003 Chenard et al.
2003/0130577 A1 7/2003 Purdy et al.
2003/0135196 A1 7/2003 Hesson et al.
2003/0163181 A1 8/2003 Frazer et al.
2003/0199802 A1 10/2003 Barbut
2004/0015133 A1 1/2004 Karim
2004/0030279 A1 2/2004 Rubenstein et al.
2004/0068221 A1 4/2004 Silverberg et al.
2004/0138125 A1 7/2004 Wang
2004/0138728 A1 7/2004 Wong et al.
2004/0142906 A1 7/2004 Wang
2004/0210231 A1 10/2004 Boucher et al.
2004/0215162 A1 10/2004 Putz
2004/0220545 A1 11/2004 Heruth et al.
2004/0254545 A1 12/2004 Rider, II et al.
2005/0004504 A1 1/2005 Frye et al.
2005/0060006 A1 3/2005 Pflueger et al.
2005/0090801 A1 4/2005 Racz et al.
2006/0015160 A1 1/2006 Lamard
2006/0030027 A1 2/2006 Ellson et al.
2006/0058836 A1 3/2006 Bose et al.
2006/0142783 A1 6/2006 Lewis et al.
2006/0175543 A1 8/2006 Elefteriades
2006/0184098 A1 8/2006 Barnitz et al.
2006/0224101 A1 10/2006 Glenn
2006/0282043 A1 12/2006 Pyles
2007/0050002 A1 3/2007 Elefteriades
2007/0246406 A1 10/2007 Dibel et al.
2007/0282303 A1 12/2007 Nash et al.
2008/0045883 A1 2/2008 Radojicic
2008/0154181 A1 6/2008 Khanna
2008/0171990 A1 7/2008 Zauner
2008/0208075 A1* 8/2008 Goldenberg ......... A61B 17/221 600/562
2008/0249458 A1 10/2008 Yamasaki
2008/0249501 A1 10/2008 Yamasaki
2008/0319376 A1 12/2008 Wilcox et al.
2009/0076357 A1 3/2009 Purdy
2009/0082800 A1 3/2009 Janardhan
2009/0157044 A1 6/2009 Liyanagama et al.
2009/0171369 A1 7/2009 Gayzik
2009/0277850 A1 11/2009 Adams et al.
2010/0030196 A1 2/2010 Hildebrand et al.
2010/0145267 A1 6/2010 Bishop et al.
2010/0168665 A1 7/2010 Skerven
2010/0179509 A1 7/2010 Pyles
2010/0198195 A1 8/2010 Nishtala et al.
2010/0204672 A1 8/2010 Lockhart et al.
2010/0260815 A1 10/2010 Kyle et al.
2010/0280438 A1 11/2010 Thomas
2010/0305492 A1 12/2010 Lad et al.
2010/0324397 A1 12/2010 Purdy
2011/0029050 A1 2/2011 Elefteriades et al.
2011/0046547 A1 2/2011 Mantle
2011/0190831 A1 8/2011 Mafi et al.
2011/0264133 A1* 10/2011 Hanlon ............... A61M 25/007 606/200
2011/0319824 A1 12/2011 Pyles
2012/0004625 A1 1/2012 Velez-Rivera
2012/0149021 A1 6/2012 Yung et al.
2012/0165757 A1 6/2012 Purdy
2012/0203142 A1 8/2012 Bedell
2012/0203290 A1 8/2012 Warren et al.
2012/0209367 A1 8/2012 Prindle et al.
2012/0253266 A1 10/2012 Qureshi et al.
2012/0302938 A1 11/2012 Browd et al.
2012/0330196 A1 12/2012 Nita
2013/0023814 A1 1/2013 Bertrand et al.
2013/0030411 A1 1/2013 Kreck et al.
2013/0035628 A1 2/2013 Garrison et al.
2013/0066331 A1 3/2013 Chitre et al.
2013/0085413 A1 4/2013 Tsamir et al.
2013/0131811 A1 5/2013 Barreiro et al.
2013/0158470 A1 6/2013 Panotopoulos
2013/0158564 A1 6/2013 Harris et al.
2013/0165903 A1 6/2013 Webler et al.
2013/0197422 A1 8/2013 Browd et al.
2013/0248450 A1 9/2013 Kenley et al.
2014/0066830 A1 3/2014 Lad et al.
2014/0166555 A1 6/2014 Dibel et al.
2014/0194840 A1 7/2014 Eckermann
2014/0276334 A1 9/2014 Eckermann
2014/0276660 A1 9/2014 Eckermann
2014/0316373 A1 10/2014 Dhall
2014/0323857 A1 10/2014 Mourad et al.
2015/0196742 A1 7/2015 Browd et al.
2015/0223832 A1 8/2015 Swaney et al.
2015/0224284 A1 8/2015 Panotopoulos et al.
2015/0238685 A1 8/2015 Elias et al.
2015/0257774 A1 9/2015 Galdonik et al.
2016/0051801 A1 2/2016 Vase
2016/0101270 A1 4/2016 Browd et al.
2016/0136398 A1 5/2016 Heilman et al.
2016/0174995 A1 6/2016 Turjman et al.
2016/0303355 A1 10/2016 Heilman et al.
2016/0303356 A1 10/2016 Heilman et al.
2017/0000361 A1 1/2017 Meyering et al.

FOREIGN PATENT DOCUMENTS

CA 101288783 A 10/2008
CA 2793672 A1 9/2011
CA 2936349 A1 7/2015
CN 101653637 A 2/2010
CN 202409608 U 9/2012
CN 102973305 A 3/2013
CN 203816046 U 9/2014
CN 203935243 U 11/2014
CN 105361923 A 3/2016
EP 0515007 B1 12/1996
EP 1331019 A2 7/2003
EP 2217315 B1 5/2012
EP 2695633 A1 2/2014
EP 2882483 B1 9/2016
GB 2365344 A 2/2002
JP 03504681 A 10/1991
JP 2001509712 A 7/2001
JP 2001513349 A 9/2001
JP 2002514096 A 5/2002
JP 2003515394 A 5/2003
JP 2003250881 A 9/2003
JP 2003526398 A 9/2003
JP 2004508109 A 3/2004
JP 2004236792 A 8/2004
JP 2004528062 A 9/2004
JP 2006525827 A 11/2006
RU 2100965 C1 1/1998
RU 2158613 C2 11/2000
RU 2290974 C1 1/2007
RU 2312678 C1 12/2007
RU 2314838 C2 1/2008
WO 8909629 A1 10/1989
WO 9205864 A1 4/1992
WO 9802202 A1 2/1998
WO 9833535 A1 8/1998
WO 9907276 A2 2/1999
WO 0041762 A1 7/2000
WO 0043056 A1 7/2000
WO 0051669 A1 9/2000
WO 0139819 A2 6/2001
WO 0211703 A1 2/2002
WO 0220083 A2 3/2002
WO 0232494 A2 4/2002
WO 03015710 A2 2/2003
WO 03020208 A2 3/2003
WO 03057306 A1 7/2003
WO 2004060463 A1 7/2004

(56) References Cited

FOREIGN PATENT DOCUMENTS

| | | | |
|---|---|---|---|
| WO | 2004072647 | A1 | 8/2004 |
| WO | 2004093945 | A1 | 11/2004 |
| WO | 2004105839 | A1 | 12/2004 |
| WO | 2005035025 | A1 | 4/2005 |
| WO | 2005044335 | A2 | 5/2005 |
| WO | 2005044847 | A1 | 5/2005 |
| WO | 2006017763 | A1 | 2/2006 |
| WO | 2006079007 | A2 | 7/2006 |
| WO | 2006086195 | A1 | 8/2006 |
| WO | 2007013945 | A2 | 2/2007 |
| WO | 2007110643 | A1 | 10/2007 |
| WO | 2008105959 | A2 | 9/2008 |
| WO | 2009140202 | A1 | 11/2009 |
| WO | 2009155614 | A2 | 12/2009 |
| WO | 2010127071 | A1 | 11/2010 |
| WO | 2010014447 | A3 | 2/2011 |
| WO | 2011060317 | A2 | 5/2011 |
| WO | 0154766 | A1 | 8/2011 |
| WO | 2011114260 | A1 | 9/2011 |
| WO | 2011150323 | A2 | 12/2011 |
| WO | 2012099984 | A1 | 7/2012 |
| WO | 2013034602 | A1 | 3/2013 |
| WO | 2013052951 | A2 | 4/2013 |
| WO | 2014023551 | A1 | 2/2014 |
| WO | 2014023552 | A1 | 2/2014 |
| WO | 2014039780 | A1 | 3/2014 |
| WO | 2014160481 | A1 | 10/2014 |
| WO | 2015104631 | A1 | 7/2015 |
| WO | 2015109260 | A1 | 7/2015 |
| WO | 2015157320 | A1 | 10/2015 |
| WO | 2016007553 | A1 | 1/2016 |

OTHER PUBLICATIONS

Enchev et al; "Historical Trends of Neuroendoscopic Surgical Techniques in the Treatment of Hydrocephalus," Neurosurgery Review, vol. 31, pp. 249-262, 2008.

Gascoyne et al; "Dielectrophoretic Separation of Cancer Cells from Blood," IEEE Transactions of Industry Applications, vol. 33, No. 3, pp. 670-678, May/Jun. 1997.

Gascoyne et al; "Isolation of Rare Cells from Cell Mixtures by Dielectrophoresis," Electrophoresis, vol. 30. No. 8, pp. 1388-1398, Apr. 2009.

Gascoyne et al; "Particle Separation by Dielectrophoresis," Electrophoresis, vol. 23, No. 13, pp. 1973-1983, Jul. 2002.

Haltiwanger, "The Electrical Properties of Cancer Cells", www.royalrife.com/haltiwanger1, 62 pages, Jul. 2010.

Han et al; "An Electrorotation Technique for Measuring the Dielectric Properties of Cells with Simultaneous Use of Negative Quadropolar Dielectrophoresis and Electrorotation," The Royal Society of Chemistry, vol. 138, pp. 1529-1537, 2013.

Helmy et al; "The Cytokine Response to Human Traumatic Brain Injury: Temporal Profiles and Evidence for Cerebral Parenchymal Production," Journal of Cerebral Blood Flow & Metabolism, vol. 31, pp. 658-670, 2011.

Huang et al; "Electrode Design for Negative Dielectrophoresis," Measurement Science and Technolgy, vol. 2, pp. 1142-1146, Dec. 1991.

Jones et al; "Multipolar Dielectrophoretic and Electrorotation Theory," Journal of Electrostatics, vol. 37, pp. 121-134, 1996.

Lau et al; "Tau Protein Phosphorylation as a Therapeutic Target in Alzheimer's Disease," Current Topics in Medicinal Chemistry, vol. 2, pp. 395-415, 2002.

Levi et al; "Clinical Application of Modest Hypothermia After Spinal Cord Injury," J. Neurotrauma, vol. 26, No. 3, Abstract (1 page) pp. 407-415, Mar. 2009.

Li et al; "Continuous Dielectrophoretic Cell Separation Microfluidic Device," The Royal Society of Chemistry, Lab Chip, vol. 7, pp. 239-248, 2007.

Madeira-Lopes et al; Comparative Study of the Temperature Profiles of Growth and Death of the Pathogenic Yeast Cryptococcus Neoformans and the non-pathogenic Cryptococcus Albidus, Journal of Basic Microbiology, vol. 26, pp. 43-47, 1986.

Markx et al; "Dielectrophoretic Separation of Bacteria Using a Conductivity Gradient," Journal of Biotechnology, vol. 51, pp. 175-180, Dec. 1996.

Markx et al; "Dielectrophoretic Separation of Cells: Continuous Separation," Biotechnology and Bioengineering, vol. 45, No. 4, pp. 337-343, Feb. 1995.

Marszalek et al; "Determination of Electrical Parameters of Cell Membranes by a Dielectrophoresis Method," Biophysical Journal, vol. 59, pp. 982-987, May 1991.

McKeating et al; "Cytokines and Adhesion Molecules in Acute Brain Injury," British Journal of Anaesthesia, vol. 80, pp. 77-84, 1998.

Misaki et al; "Contrast-Enhanced Fluid-Attenuated Inversion Recovery MRI is useful to Detect the CSF Dissemination of Glioblastoma," Journal of Computer Assisted Tomography, vol. 25, No. 6, pp. 953-956, 2001.

Morganti-Kossman et al; "Production of Cytokines Following Brain Injury: Beneficial and Deleterious for the Damaged Tissue," Molecular Psychiatry, vol. 2, pp. 133-136, 1997.

Onda et al; "Cerebral Glioblastoma with Cerebrospinal Fluid Dissemination: a Clinicopathological Study of 14 Cases Examined by Complete Autopsy," Neurosurgery, vol. 25, No. 4, pp. 533-540, 1989.

Park et al; "3-D Electrode Designs for Flow-Through Dielectrophoretic Systems," Electrophoresis, vol. 26, pp. 3745-3757, 2005.

Park "Continuous Dielectrophoretic Bacterial Separation and Concentration from Physiological Media of High Conductivity" The Royal Society of Chemistry, Lab Chip, vol. 11, pp. 2893-2900, 2011.

Perfect, "Cryptococcus Neoformans: the Yeast that Likes it Hot," FEMS Yeast Res; vol. 6, pp. 463-468, 2006.

Pethig et al; "Applicants of Dielectrophoresis in Biotechnology," Tibtech, vol. 15, pp. 426-432, Oct. 1997.

Pethig, "Dielectrophoresis: Status of the Theory, Technology, and Applications," Biomicrofluidics, vol. 4, pp. 022811-1-02281-35, 2010.

Pethig, "Dielectrophoresis: Using Inhomogeneous AC Electrical Fields to Separate and Manipulate Cells," Critical Reviews in Biotechnology, vol. 16, No. 4, pp. 331-348, 1996.

Polderman et al; "Therapeutic Hypothermia and Controlled Normothermia in the Intensive Care Unit: Practical Considerations, Side Effects, and Cooling Methods," Crit. Care Med; vol. 37, No. 3, Abstract (1 page), Mar. 2009.

Reiber, "Proteins in cerebrospinal fluid and blood: Barriers, CSF flow rate and source-related dynamics", Restorative Neurology and Neuroscience, vol. 21, pp. 79-96, 2003.

Stephens et al; "The Dielectrophoresis Enrichment of CD34 Cells from Peripheral Blood Stem Cell Harvests," vol. 18, pp. 777-782, 1996.

Tay et al; "Electrical and Thermal Characterization of a Dielectrophoretic Chip with 3D Electrodes for Cells Manipulation," Electrochimica. Acta; vol. 52, pp. 2862-2868, 2007.

Author Unknown, "External CSF Drainage," Aqueduct Neurosciences, (2 pages), Jul. 2014.

Author Unknown, "Therapeutic Hypothermia for Spinal Cord Injury," Crit. Care Med. vol. 37, Supp. 7, Abstract (1 page), Jul. 2009.

Author Unknown, "LiquoGuard", Moller Medical, Brochure, 2 pages, published on or before 2015.

Author Unknown, World Journal of Radiology, vol. 4, No. 6, pp. 241-290, Jun. 28, 2012.

Voldman, "Electrical Forces for Microscale Cell Manipulation," Annu. Rev. Biomed. Eng; vol. 8, pp. 425-454, 2006.

Weis et al; "Noninvasive Monitoring of Brain Temperature During Mild Hypothermia," vol. 27, No. 7, Abstract (1 page), Sep. 2009.

Ziebell et al; Involvement of Pro- and Anti-Inflammatory Cytkines and Chemokines in the Pathophysiology of Traumatic Brain Injury, Neurotherapeutics: the Journal of the American Society for Experimental NeuroTherapeutics, vol. 7, pp. 22-30, Jan. 2010.

European Office Action for European Patent Application No. 07873762.4, dated Dec. 7, 2016 (5 pages).

(56) References Cited

OTHER PUBLICATIONS

Mahon et al; North American Clinical Experience with the EKOS MicroLysUS Infusion Catheter for the Treatment of Embolic Stroke, AJNR Am J. Neuroradiology, vol. 24, pp. 534-538, Mar. 2003.
Rogers et al; "Percutaneous aspiration of brain tumor cysts via the Ommaya reservoir system," Neurology, vol. 41, pp. 279-282, Feb. 1991.
Siddiqui et al; "Use of the Penumbra System 054 plus Low Dose Thrombolytic Infusion for Multifocal Venous Sinus Thrombosis," Interventional Neuroradilogy, vol. 18, pp. 314-319, 2012.
Spiegelberg GmbH & Co. KG, "EVD-Catheters," downloaded on Nov. 3, 2016 from website, http://www.spiegelberg.de/products/drainage/silverline_evd_catheter_3001002.html (1 page).
Wagner et al; "Ultra-early clot aspiration after lysis with tissue plasminogen activator in a porcine model of intracerebral hemororrhage: edema reduction and blood-brain barrier protection," J. Neurosurg; vol. 90, pp. 491-498, Mar. 1999.
Ziu et al; "A Series of Cerebral Venous Sinus Thromboses Treated with Intra-Arterial tPA infused over Ten Hours with a 0.027-inch Catheter and Literature Review," pp. 1-13, Jun. 23, 2016.
International Search Report and Written Opinion for International Application PCT/US2016/036626, mailed Sep. 3, 2016 (12 pages).
European Search Report and Opinion for European Patent Application No. 07873762.4 dated May 27, 2011 (11 pages).
International Search Report and Written Opinion of the International Searching Authority for International Patent Application No. PCT/US2010/01186, mailed Jun. 21, 2010 (7 pages).
International Search Report and Written Opinion of the International Searching Authority for International Patent Application No. PCT/US2007/80834, mailed Oct. 28, 2008 (8 pages).
Banci, et al; "Metal-free superoxide dismutase forms soluble oligomers under physiological conditions: a possible general mechanism for familial ALS," PNAS, vol. 104, No. 27, pp. 11263-11267, Jul. 3, 2007.
Bayer et al; "Evaluation of the safety and immunogenicity of synthetic AB42 (AN1792) in patients with AD," Neurology, vol. 64, pp. 94-101, Jan. 2005.
Blennow et al; "Alzheimer's disease," Lancet, vol. 368, pp. 387-403, Jul. 29, 2006.
Caughey et al, "Protofibrils, pores, fibrils and neurodegeneration: separating the responsible aggregates from the innocent bystanders," Annu. Rev. Neurosci. vol. 26, pp. 267-298, 2003.
Dawson et al; "Molecular Pathways of Neurodegeneration in Parkinson's Disease," Science, vol. 302, pp. 819-822, Oct. 21, 2003.
Dekosky et al; "Looking Backward to Move Forward: Early Detection of Neurodegenerative Disorders," Science, pp. 830-834, Oct. 31, 2003.
Dias-Santagata et al; "Oxidative stress mediates tau-induced neurodegeneration in *Drosophila*", Journal of Clinical Investigation, vol. 117, pp. 236-245, Jan. 2007.
Dunnett et al; "Prospects for new restorative and neuroprotective treatments in Parkinson's disease", Nature, vol. 399, pp. A32-A38, SUPP, Jun. 24, 1999.
Gilman et al; "Clinical effects of Aβ immunization (AN1792) in patients with AD in an interrupted trial," Neurology, vol. 64, pp. 1553-1562, May 2005.
Glabe, "Common mechanisms of amyloid oligomer pathogenesis in degenerative disease," Neurobiology of Aging, vol. 27, pp. 570-575, 2006.
Hansson et al; "Association between CSF biomarkers and incipient Alzheimer's disease in patients with mild cognitive impairment: a follow-up study," Lancet Neurol; vol. 5, pp. 228-234, Mar. 2006.
Hock et al; "Antibodies against beta-amyloid slow cognitive decline in Alzheimer's disease," Neuron, vol. 38, pp. 547-554, May 22, 2003.
Hohlfeld et al; "Autoimmune concepts of multiple sclerosis as a basis for selective immunotherapy: From pipe dreams to (therapeutic) pipelines," PNAS, vol. 101, Suppl. 2, pp. 14599-14606, Oct. 5, 2004.
Janus et al; "A beta peptide immunization reduces behavioral impairment and plaques in a model of Alzheimer's disease," Nature, vol. 408, pp. 979-982, Dec. 2000.
Kessler et al; "Endothelin- 1 levels in plasma and cerebrospinal fluid of patients with cerebral vasospasm after aneurysmal subarachnoid hemorrhage," Surgical Neurology, vol. 64, pp. S1:2-S1:5, 2005.
Koo et al; "Amyloid diseases: Abnormal protein aggregation in neurodegeneration," Proc. Natl. Acad. Sci; vol. 96, pp. 9989-9990, Aug. 1999.
Kuwabara et al; "Intravenous immunoglobin therapy for Guillan-Barre syndrome with IgG anti-GM1 antibody," Muscle & Nerve, pp. 53-58, Jan. 2001.
MacDonald et al; "Cerebral vasospasm after subarachnoid hemorrage: the emerging revolution," Nature Clinical Practice, Neurology, vol. 3, No. 5, pp. 256-263, May 2007.
Mascia et al; "Temporal Relationship Between Endothelin-1 Concentrations and Cerebral Vasospasm in Patients With Aneurysmal Subarachnoid Hemorrhage-Editorial Comment: Endothelin-1 in Vasospasm After SAH," Stroke, pp. 1185-1190, May 2001.
McCulloch et al; "A radical approach to stroke therapy," PNAS, vol. 98, No. 20, pp. 10989-10991, Sep. 25, 2001.
McKhann et al; "Plasmapherisis and Guillain-Barre syndrome: analysis of prognostic factors and the effect of plasmapheresis," Annals of Neurology, vol. 23, No. 4, pp. 347-353, Apr. 1988.
Melnikova, "Therapies for Alzheimer's disease," Nature Reviews, vol. 6, pp. 341-342, May 2007.
Monsonego et al; "Immunotherapeutic Approaches to Alzheimer's Disease", Science, vol. 302,pp. 834-838, Oct. 31, 2003.
Morgan et al; "A beta peptide vaccination prevents memory loss in an animal model of Alzheimer's disease," Nature, vol. 408, pp. 982-985, Dec. 2000.
Nicoll et al; "Abeta species removal after abeta42 immunization," Journal of Neuropathology Exp. Neurol; vol. 65, No. 11, pp. 1040-1048, Nov. 2006.
Noseworthy, "Progress in determining the causes and treatment of multiple sclerosis," Nature, vol. 399, Supp., pp. A40-A47, Jun. 24, 1999.
Orogozo et al; "Subacute meningoencephalitis in a subset of patients with AD after Aβ42 immunization," Neurology, vol. 61, pp. 46-54, Jul. 2003.
Parkhill et al; "The genome sequence of the food-borne pathogen *Campylobacter jejuni* reveals hypervariable sequences," Nature, vol. 403, pp. 665-668, Feb. 10, 2000.
Roberson et al; "100 Years and Counting: Prospects for Defeating Alzheimer's Disease," Science, vol. 314, pp. 781-784, Nov. 3, 2006.
Rowland, "Amyotrophic Lateral Sclerosis: Human Challenge for Neuroscience," Proc. Natl. Acad. Sci; vol. 92, pp. 1251-1253, Feb. 1995.
Shoulson, "Experimental Therapeutics of Neurodegenerative Disorders: Unmet Needs," Science, vol. 282, pp. 1072-1074, Nov. 6, 1998.
Steece-Collier et al; "Etiology of Parkinson's disease: Genetics and environment revisited," PNAS, vol. 99, No. 22, pp. 13972-13974, Oct. 29, 2002.
Taylor et al; "Toxic Proteins in Neurodegenerative Disease," Science, vol. 296, pp. 1991-1995, Jun. 14, 2002.
Valentine et al; "Misfolded CuZnSOD and amyotrophic lateral sclerosis," PNAS, vol. 100, No. 7, pp. 3617-3622, Apr. 1, 2003.
Vernino et al; "Autoimmune encephalopathies," The Neurologist, vol. 13, No. 3, May 2007.
Wollinsky et al; CSF filtration is an effective treatment of Guillan-Barre syndrome: a randomized clinical trial, Neurology, vol. 57, pp. 774-780, Sep. 2001.
Yuki et al; "Carbohydrate mimicry between human ganglioside GM1 and Campylobacter Jejuni lipooligosaccaride causes Guillain-Barre syndrome," PNAS, vol. 101, No. 31, pp. 11404-11409, Aug. 3, 2004.
Japanese Rejection of Appeal for related Japanese Patent Application No. 2009-531646, mailed Jan. 25, 2016 (13 pages).
Arnold et al; "Electro-Rotation: Development of a Technique for Dielectric Measurements on Individual Cells and Particles." Journal of Electrostatics, vol. 21, pp. 151-191, 1988.

(56) References Cited

OTHER PUBLICATIONS

Arvin et al; "The Role of Inflammation and Cytokines in Brain Injury," Neuroscience and Biobehavorial Reviews, vol. 20, No. 3, pp. 445-452, 1996.
Becker et al; "Separation of Human Breast Cancer Cells from Blood by Differential Dielectric Affinity," Proc. Natl. Acad. Sci, vol. 92, pp. 860-864, Jan. 1995.
Becker et al; "The Removal of Human Leukemia Cells for Blood Using Interdigitated Microelectrodes," J. Phys. D: Appl. Phys; vol. 27, pp. 2659-2662, 1994.
Buzzigoli et al; "Plasmapherisis treatment in Guillain-Barre syndrome: potential benefit over intravenous immunoglobin," Anaesth Intensive Care, vol. 38, No. 2, pp. 387-389, Abstract (1 page) Mar. 2010.
Cambria et al; "Clinical Experience with Epidural Cooling for Spinal Cord Protection during Thoracic and Thoracoaabdominal Aneurysim Repair," Journal of Vascular Surgery, vol. 25, No. 2, pp. 234-243, Feb. 1997.
Cook, "Combined Spinal-Epidural Techniques," Anaesthesia, vol. 55, pp. 42-64, 2000.
Covaciu et al; "Brain Temperature in Volunteers Subjected to Intranasal Cooling," Intensive Care Med; vol. 37, No. 8, Abstract (1 page) 1277-1284, Aug. 2011.
Delhaas, "Extradural and Subarachnoid Catheterization Using the Seldinger Technique," British Journal of Anaesthesia, vol. 76, pp. 149-150, 1996.

* cited by examiner

Fig. 35
Fig. 36
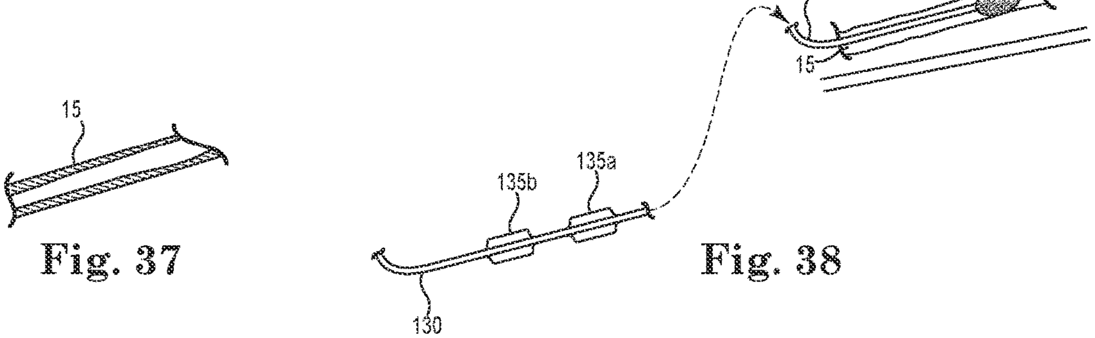
Fig. 37
Fig. 38

SURFACE AREA COMPARISONS (DISTAL/OUTLET)

| PROTOTYPES | DISTAL/OUTLET AREA ($mm^2$) | DISTAL/OUTLET AREA ($IN^2$) |
|---|---|---|
| FIG 12A | 0.84949 | 0.00132 |
| FIG 12B | 0.84949 | 0.00132 |
| FIG 12C | 0.54193 | 0.00084 |
| FIG 12D | 0.20268 | 0.00031 |
| FIG 12E | 0.20268 | 0.00031 |
| FIG 12F | 0.41935 | 0.00065 |
| FIG 12G | 0.02452 | 0.00038 |
| 2Fr KNOWN | 0.26805 | 0.00042 |
| 3Fr KNOWN | 0.65669 | 0.00102 |
| 4Fr KNOWN | 1.21660 | 0.00189 |
| 5Fr KNOWN | 1.94778 | 0.00302 |

Fig. 58

SURFACE AREA COMPARISONS (PROXIMAL/INLET)

| PROTOTYPES | PROX/INLET AREA ($mm^2$) | PROX/INLET AREA ($in^2$) |
|---|---|---|
| FIG 12A | 0.97287 | 0.00151 |
| FIG 12B | 1.61132 | 0.00250 |
| FIG 12C | 0.54193 | 0.00084 |
| FIG 12D | 0.74193 | 0.00115 |
| FIG 12E | 0.92903 | 0.00144 |
| FIG 12F | 0.83871 | 0.00130 |
| FIG 12G | 0.97419 | 0.00151 |
| 2Fr KNOWN | 0.26805 | 0.00042 |
| 3Fr KNOWN | 0.65669 | 0.00102 |
| 4Fr KNOWN | 1.21660 | 0.00189 |
| 5Fr KNOWN | 1.94778 | 0.00302 |

Fig. 59

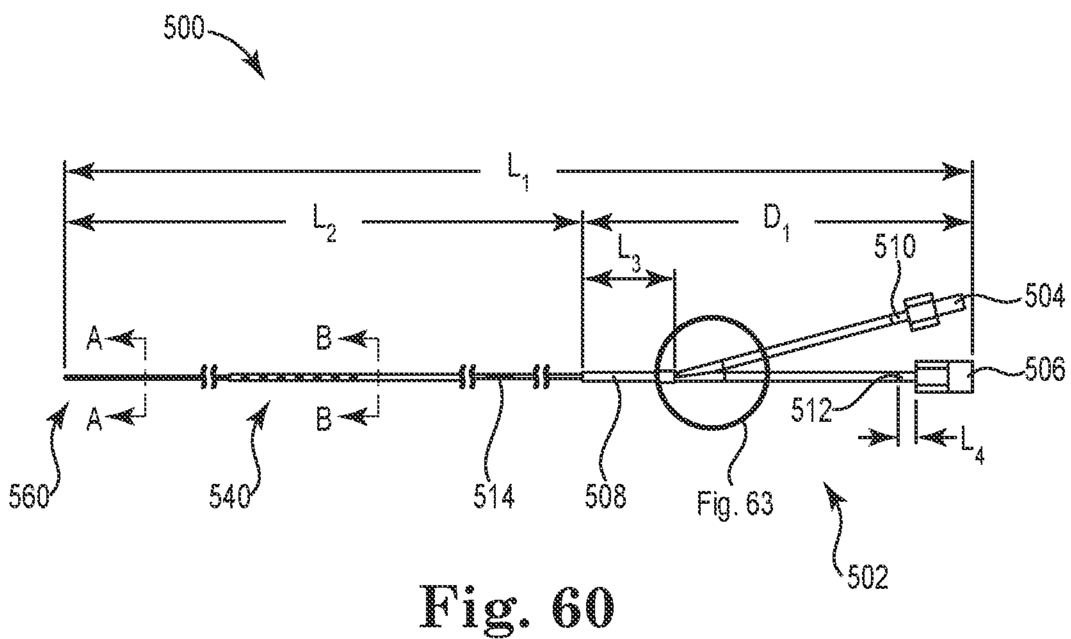
Fig. 60
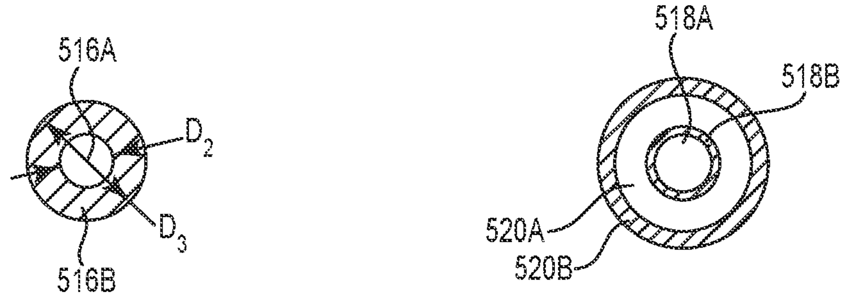
Fig. 61
Fig. 62
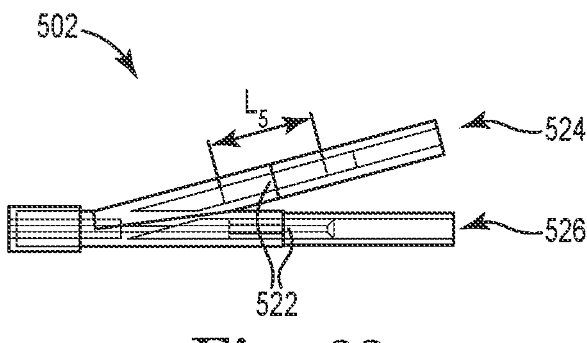
Fig. 63

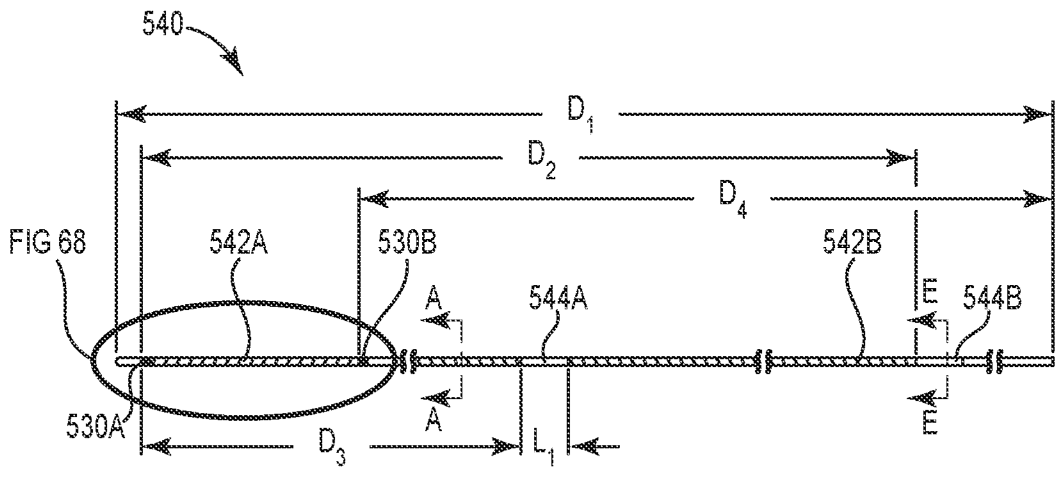
Fig. 67
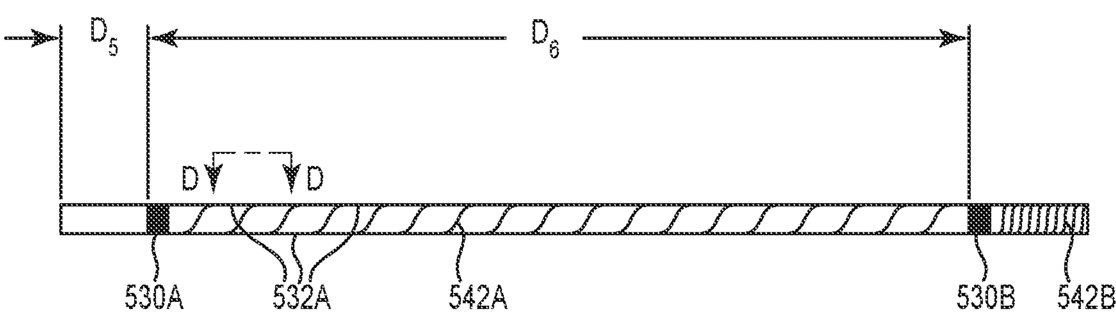
Fig. 68
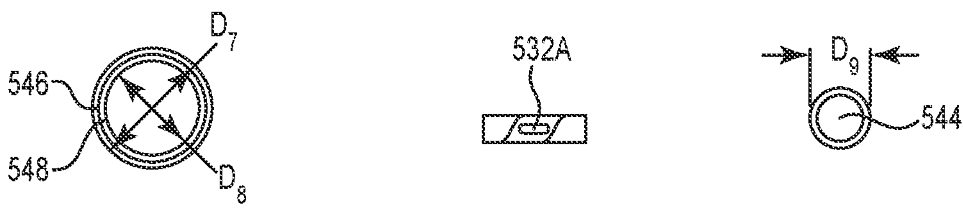
Fig. 69
Fig. 70
Fig. 71

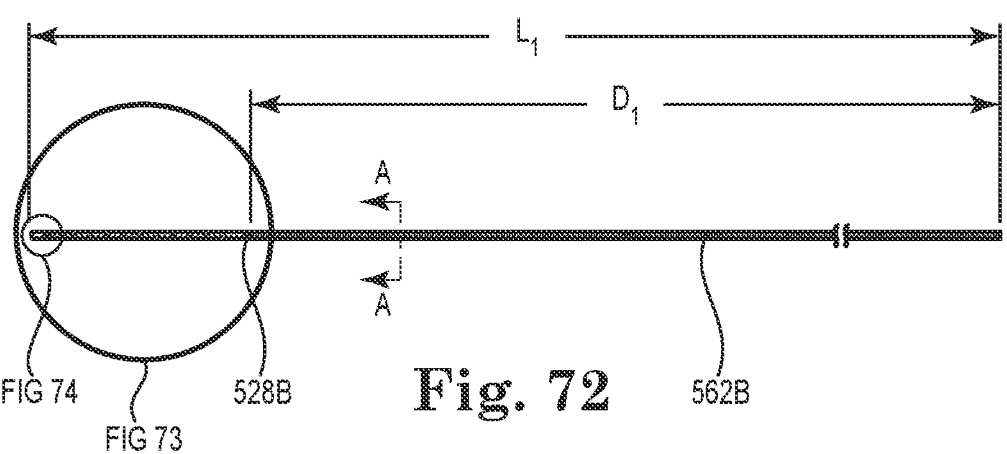
Fig. 72
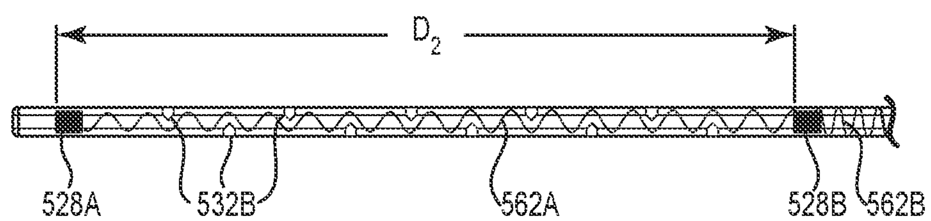
Fig. 73
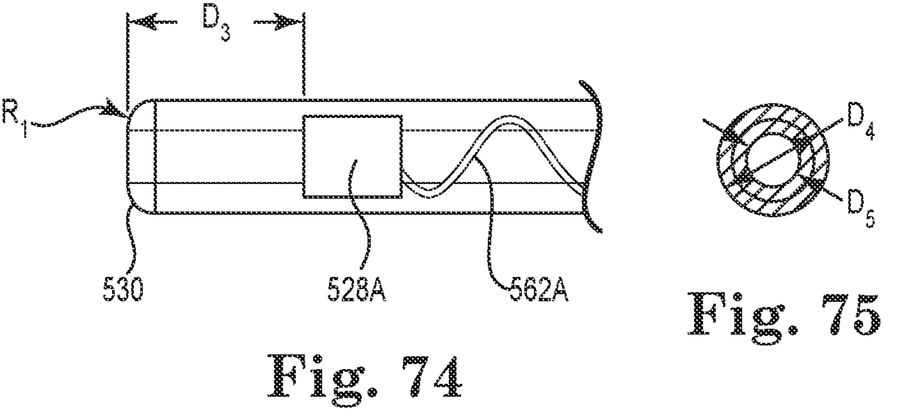
Fig. 74
Fig. 75

DEVICES AND SYSTEMS FOR ACCESS AND NAVIGATION OF CEREBROSPINAL FLUID SPACE

CROSS-REFERENCE TO RELATED APPLICATION

This application is a continuation of U.S. application Ser. No. 14/743,652 filed Jun. 18, 2015 which claims the benefit of U.S. Provisional Application No. 62/038,998, filed on Aug. 19, 2014, entitled "Devices and Systems for Access and Navigation of Cerebrospinal Fluid Space, the contents of which are incorporated herein by reference in their entirety.

TECHNICAL FIELD

The present disclosure relates to systems, devices and methods for access and navigation of the cerebrospinal fluid space surrounding the brain and the spinal column.

BACKGROUND

Cerebrospinal fluid (CSF) is a generally clear, colorless fluid that is produced in the ventricles, specifically the choroid plexuses, in the brain. The choroid plexus produces approximately 500 milliliters of CSF daily in order to accommodate flushing or recycling of CSF to remove toxins and metabolites, which happens several times per day. From the choroid plexus, CSF flows slowly through a channel (canal) into the spinal column, and then into the body. CSF is found in the space between the pia mater and the arachnoid mater, known as the subarachnoid space. CSF is also found in and around the ventricular system in the brain, which is continuous with the central canal of the spinal cord. In the event of a stroke or other brain trauma, it can be desirable to remove the CSF from one location (e.g., the cervical region of the spine, or a brain ventricle), filter it, and return it to the CSF space at a second location (e.g., the lumbar region of the spine). U.S. Pat. No. 8,435,204 provides background relevant to the present disclosure, and is hereby incorporated by reference in its entirety for all purposes.

However, accurate delivery of medical instruments to the CSF space can be challenging.

Against this backdrop, the present disclosure was developed.

The information included in this Background section of the specification, including any references cited herein and any description or discussion thereof, is included for technical reference purposes only and is not to be regarded subject matter by which the scope of the invention is to be bound.

SUMMARY

Aspects of the present disclosure address the aforementioned needs by providing systems, devices and methods for the access and navigation of the cerebrospinal fluid space.

A system for access and navigation of a CSF space is disclosed. In one aspect, the system includes a curved introducer sheath having a radius of curvature configured to access and align with the cerebrospinal fluid space and an introducer coupled to a proximal end of the curved introducer sheath. In one embodiment, the introducer may have a plurality of ports, which may have a valve, such as a check valve, operably associated therewith. The system also may include a curved catheter, which may have multiple lumens and which may be configured to be received in the curved introducer.

One or more sensors or transducers may be positioned on or about the catheter. In one embodiment, at least one transducer may be a pressure sensor and at least one transducer may be a flow sensor, or one or more transducers may sense both and/or other properties. Upon delivery of the catheter through the introducer and the introducer sheath, the catheter is positioned to access and navigate the cerebrospinal fluid space.

In some aspects, the curved catheter may include a spring loaded tip, which may be in a pre-deployed position during delivery through the introducer sheath and in a deployed position after exiting the introducer sheath. In some aspects, the system may include a strain relief and/or kink resistance feature, which may be formed as a sleeve and disposed on the curved catheter (e.g., at a failure point of the curved catheter). In some aspects, the strain relief and kink resistance feature may be a coiled or a braided wire, which may be embedded in a tube comprising medical grade catheter material, such as silicone, nylon, polyurethane, aromatic polyether-based thermoplastic polyurethanes, or polyether block amide.

In some aspects, the system may include a plurality of openings defined within an outer circumferential wall of the catheter to increase fluid flow through the system. The plurality of openings may have a suitable total cross-sectional surface area, for example, at least about 0.6 $mm^2$. The plurality of openings may be positioned generally linearly along or parallel to a horizontal line defined through a central lumen of the catheter. The plurality of openings may be positioned randomly, or in a pattern, such as a staggered or symmetrical pattern, relative to a horizontal line defined through a central lumen of the catheter. In some aspects, one or more openings are defined within an outer circumferential wall one of an inlet lumen or an outlet lumen of the catheter to increase fluid flow through the system. In some aspects, at least one of the one or more openings defined within the outer circumferential wall of the inlet lumen has a total cross-sectional surface area of less than 0.01 $in^2$. In some aspects, at least one of the one or more openings defined within the outer circumferential wall of the outlet lumen has a total cross-sectional surface area of approximately 0.01 $in^2$. In certain implementations, the size of the lumen, material thickness generally, and/or other configurations of the catheter may be selected or configured to enhance the catheter's capability to unblock an opening and/or resist blockages of an opening. For example, in certain implementations, the inner wall of a lumen may have an inner diameter of approximately 0.56 mm and an outer diameter of approximately 0.71 mm, and the outer wall of the lumen may have an inner diameter of approximately 1.32 mm and an outer diameter of approximately 1.689 mm, however, other configurations are possible.

In some aspects, the system may further include a receptacle to capture and retrieve blood clots within the CSF space. In some embodiments, the receptacle may include a coiled microwire configured for delivery through the catheter to capture and retrieve a blood clot within the CSF space. In some embodiments, the receptacle comprises a plurality of intertwined microwires configured for delivery through the catheter to capture and retrieve a blood clot within the CSF space. In some embodiments, the receptacle may include a sieve coupled to a distal end of a microcatheter and configured for delivery through the catheter to capture and retrieve a blood clot within the CSF space. Combinations of these and/or other structures also may be used.

In some aspects, the system may include a positioning device. In one embodiment, a positioning device may comprise a plurality of lumens and a plurality of balloons. Each balloon may be positioned in an individual lumen in a deflated state during delivery of the positioning device through the curved introducer sheath. The balloon may transition from a deflated state to in an inflated state and back to a deflated state during advancement of the system into the CSF space.

In some aspects, the cerebrospinal fluid space is a space where cerebrospinal fluid flows around in or through a ventricle of the brain or the cerebrospinal fluid space is a space where cerebrospinal fluid flows around in or through a spinal column.

Methods of accessing and navigating a CSF space are disclosed. One method includes introducing a curved introducer sheath having a radius of curvature, aligning the introducer sheath with the CSF space, and deploying a curved catheter having multiple lumens into the curved introducer sheath through a multi-port introducer coupled to a proximal end of the curved introducer sheath. The curved catheter may have one or more transducers positioned on or about the catheter to detect properties such as pressure, flow, and other properties. One method includes delivering the catheter through an access site in the CSF space created by the curved introducer sheath and positioning the catheter to access and navigate the CSF space. In some aspects, the CSF space is a space where cerebrospinal fluid flows around a ventricle of the brain. In some aspects, the CSF space is a space where cerebrospinal fluid flows around a spinal column.

In certain implementations, the catheter may have a length of between approximately 40 cm and approximately 120 cm and the catheter may comprise an inlet opening and an outlet opening. The inlet opening and the outlet opening may have a spacing of between approximately 10 cm and approximately 30 cm. In certain implementations, multiple lumens may comprise a first lumen defined by an inner wall and a second lumen defined between the inner wall and an outer wall. The inner wall may have an inner diameter of approximately 0.56 mm and an outer diameter of approximately 0.71 mm. The outer wall may have an inner diameter of approximately 1.32 mm and an outer diameter of approximately 1.689 mm. In certain implementations, the catheter comprises a coiled wire having a coil pitch selected to enable the catheter to be deployed and positioned without kinking or compromising flow within the catheter and to enable catheter unblocking. In certain implementations, the coil pitch may be between approximately 0.01" and approximately 0.03".

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Other features, details, utilities, and advantages of the present invention will be apparent from the following more particular written description of various embodiments of the invention as further illustrated in the accompanying drawings and defined in the appended claims.

BRIEF DESCRIPTION OF THE DRAWINGS

The present disclosure, both as to its organization and manner of operation, may be understood by reference to the following description, taken in connection with the accompanying drawings, in which:

FIGS. 35 through 38 depict an embodiment of a positioning device with one or more inflatable balloons for use with the system of FIG. 1;

FIGS. 58 and 59 depict a comparison between various embodiments of the lumens disclosed herein and known lumens;

FIG. 60 illustrates a Y-connector portion, a proximal subassembly, and a distal subassembly of a catheter according to certain implementations;

FIG. 61 illustrates a sectional view taken from the region of the catheter of FIG. 60 marked with cutting plane line A-A;

FIG. 62 illustrates a sectional view taken from the region of the catheter of FIG. 60 marked with cutting plane line B-B;

FIG. 63 illustrates an enlarged, detail view of a portion of the Y-connector of the catheter of FIG. 60;

FIG. 67 illustrates a portion of a proximal subassembly according to certain implementations;

FIG. 68 illustrates a detail view of the proximal subassembly of FIG. 67;

FIG. 69 illustrates a sectional view taken from the region of the proximal subassembly of FIG. 67 marked with the cutting plane line A-A;

FIG. 70 illustrates a detail view of a portion of the proximal subassembly of FIG. 68 taken from the view of line D-D;

FIG. 71 illustrates a sectional view taken from the region of the proximal subassembly of FIG. 67 marked with the cutting plane E-E;

FIG. 72 illustrates a portion of a distal subassembly according to certain implementations;

FIG. 73 illustrates a detailed portion of the distal subassembly of FIG. 72;

FIG. 74 illustrates a detailed portion of the distal subassembly of FIG. 72; and FIG. 75 illustrates a sectional view taken from the region of the distal subassembly of FIG. 72 marked with the cutting plane A-A.

DETAILED DESCRIPTION

Figure 1:
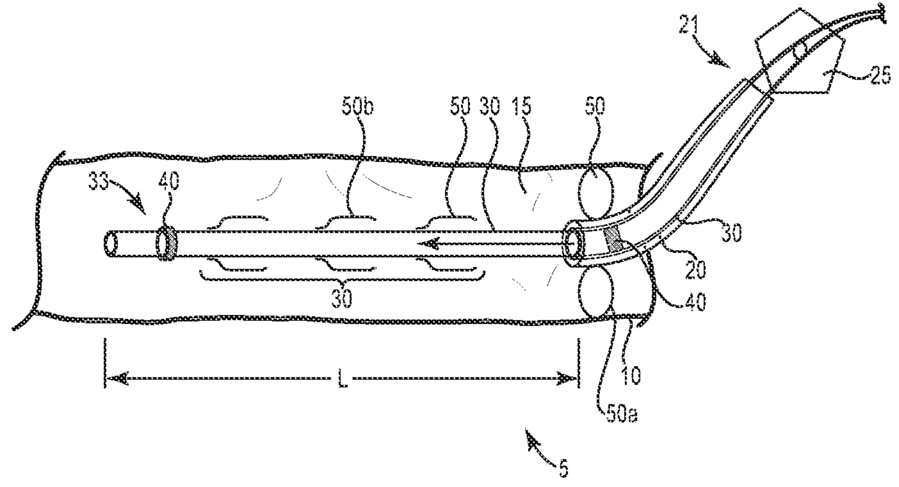
FIG. 1 depicts aspects of a system for access and navigation of the cerebrospinal fluid space in accordance with the present disclosure.

The present disclosure relates to removal, exchange and recirculation of cerebrospinal fluid (CSF). Devices, systems and methods disclosed herein are used to safely and efficiently navigate the space at and around the brain and spinal cord where the CSF flows through the body, also known as the CSF space. Specialized devices and systems are useful and sometimes necessary to navigate the CSF space due to the difficult points of entry and exit and the potentially life threatening consequences if a mistake is made. Increased safety and efficacy reduce time spent in the surgical suite and potential complications.

Neuropheresis is the removal of blood from CSF. This and other therapeutic techniques can be used to treat a number of neurological diseases or conditions, such as Alzheimer's Disease, Parkinson's Disease, Huntington's Disease, Amyotrophic Lateral Sclerosis (ALS), Encephalitis from various causes, Meningitis from various causes, Guillain Barre Syndrome (GBS), Multiple Sclerosis (MS), Spinal Cord Injury, Traumatic Brain Injury, cerebral vasospasm, stroke and other diseases or conditions as described in previously mentioned U.S. Pat. No. 8,435,204.

The purification, conditioning, and/or compound removal schema can be tailored to a specific disease or group of diseases as suitable, including based on a number of features, such as size, affinity, biochemical properties, temperature, and other features. Purification schema may be based on diffusion, size-exclusion, ex-vivo immunotherapy using immobilized antibodies or antibody fragments, hydrophobic/hydrophilic, anionic/cationic, high/low binding affinity, chelators, anti-bacterial, anti-viral, anti-DNA/RNA/amino acid, enzymatic, and magnetic and/or nanoparticle-based systems. The system can be adjustable to a broad range of biologic parameters and flows.

With regard to a neuropheresis system in particular, the disclosed system can be used to safely and quickly access the CSF space with minimal disturbance to the CSF flow. The systems and devices disclosed herein provide a safe a rapid flow circuit and provide filtration by reducing the number of red blood cells in the circuit and providing for blood clot identification and removal.

A neuropheresis system should provide for the exchange, removal, and/or recirculation of CSF, safely and efficiently. The systems and devices disclosed herein may be used in a neuropheresis system. Previously described single lumen catheter systems produce only a local eddy, with minimal mixing and therefore recirculation of previously processed CSF. Such single lumen systems do not generate enough mixing to adequately draw or circulate fluid from the CSF space. The rate of mixing, the amount of new CSF turned over per minute, and the access provided to turning over the cranial and spinal CSF volume multiple times using the present invention results in a much more rapid, efficient, and feasible CSF processing system that may provide access to up to the entire CSF system. The system may provide for an adjustable distance between the inflow and outflow areas, to provide enhanced ability to mix and circulate CSF.

The systems and devices disclosed herein can be used to access the CSF space to remove the CSF from one location (e.g., the cervical region of the spine, or a brain ventricle), filter or otherwise treat it, and return it to the CSF space, including at a second location (e.g., the lumbar region of the spine), safely and efficiently. In various aspects, the systems and devices disclosed herein maintain the endogenous intracranial or intraspinal pressure within a physiological range, for example, from about 5 to about 20 mm Hg or from about 0 to about 10 mm Hg or from about −5 to about 10 mm Hg or from about −5 to about 25 mm Hg. The present system thus reduces spinal headache, for example, due to hydrocephalus (abnormal accumulation of CSF in the ventricles of the brain). In some aspects, the system may include sensors within the catheter or within the flow circuit to detect clogs or blockages in the system, thereby providing closed loop pressure control. In various aspects, the systems and devices disclosed herein also help the system to perform efficiently by reducing or eliminating recirculating flow loops. The systems and devices maintain spacing between the inlet and outlet, for example, between about 10 cm to about 40 cm. In certain implementations, the spacing is between about 10 cm and about 30 cm. The inlets and outlets are located in places in the CSF space so that turning on the pump or otherwise creating positive or negative pressure in the system will not cause or encourage tissue being drawn into the catheter. In some aspects, the inlets and outlets are placed near the lumbar cervical cisterns to prevent tissue from being drawn into the catheter. In some aspects, there may also be multiple holes along the inlet and outlet for redundancy in case there is tissue blocking some number of holes. In certain implementations, a particular coil pitch of a coiled wire within the catheter may be selected in order to facilitate catheter unblocking and/or the ability of the catheter to resist blockage. In certain aspects, the inlet-outlet spacing may be selected to be maximized while staying below the level of a cervical region of a patient. In certain aspects, the inlet-outlet spacing may be selected based on vertebral spacing. For example, the spacing may be selected so that the inlet-outlet spacing is between the lengths of approximately 5 vertebrae and approximately 12 vertebrae. In certain implementations, a spacing of approximately 10 vertebrae may be selected; however, other configurations (such as those described elsewhere in the specification) may be utilized. When designing such spacing, it may be assumed that a vertebra is approximately 2-3 cm in length, however, other measurements and designs may be used. In certain implementations, a particular size, shape, and/or other configuration of a lumen may be selected to facilitate catheter unblocking and/or the ability of the catheter to resist blockage. For example, a proximal outer diameter of a lumen of between approximately 0.060 inches and approximately 0.070 inches and a proximal inner diameter of between approximately 0.025 inches and 0.060 inches may be selected; however, other configurations (such as those described elsewhere in the specification) may be utilized.

The disclosed systems and devices are used to access the CSF space and may be used at any access point in the cervical (C1-C7), thoracic (T1-T12), or lumbar region (L1-L5) of the vertebral column. An access site in the cervical region may be used to access the ventricular system in the brain. In one embodiment, the system and device are used to access the lumbar region. In some embodiments, the inlets and outlets are located in places in the spine such that the drainage process will not cause tissue to be drawn into the catheter. For example, when a patient is lying on a table, entry may be made at a suitable angle, such as, for example, about 90 degrees, to access the spine. A traditional catheter must be pushed through a 90 degree bend at the L4-L6 region. The catheters and related delivery devices disclosed herein may be curved such that they can access and navigate this angled bend more easily and efficiently.

For a discussion of the systems and devices that provide access to and help to navigate the CSF space for CSF filtration, removal and exchange, reference is now made to FIGS. 1-59.

FIG. 1 illustrates one embodiment of the disclosed system and devices for CSF access and navigation. The CSF access and navigation system 5 includes a curved introducer sheath 20 specifically designed to access the CSF space 15. The system 5 is shown being introduced into the lumbar region 10 of a patient. The introducer sheath 20 may be a single lumen, dual-lumen, or multi-lumen device. In one embodiment, the proximal end 21 of the introducer sheath 20 may include a multi-port introducer 25, and each port may have a valve, such as a hemostasis valve or a one way valve, to prevent CSF or other fluid from passing through the port. Once the introducer 20 is inserted into the patient, a catheter 30 may be inserted into the introducer 20. The catheter 30 may be curved, to complement the introducer 20. In some embodiments, disposed on or within the catheter 30 are sensors 40, such as flow and/or pressure sensors 40, and/or sensors for other properties, such as temperature. In some aspects, the system 5 may also include a separate catheter with a basket or other receptacle at its distal end to capture and remove debris, such as a blood clot. In some embodiments, the system 5 also includes a multi-lumen device having inflatable balloons to advance the catheter 30 into the spinal canal and the CSF space 15. In some embodiments, balloons 50 may be co-located with or disposed about the catheter 30 and may be anchoring balloons 50*a* or annular balloons 50*b*. The balloons 50 are configured to stabilize the catheter during use. In some embodiments, the balloons may be radiopaque to provide increased visualization of the catheter 30 within the CSF space.

Curved Introducer Sheath

Figures 2, 3, 5, 6:
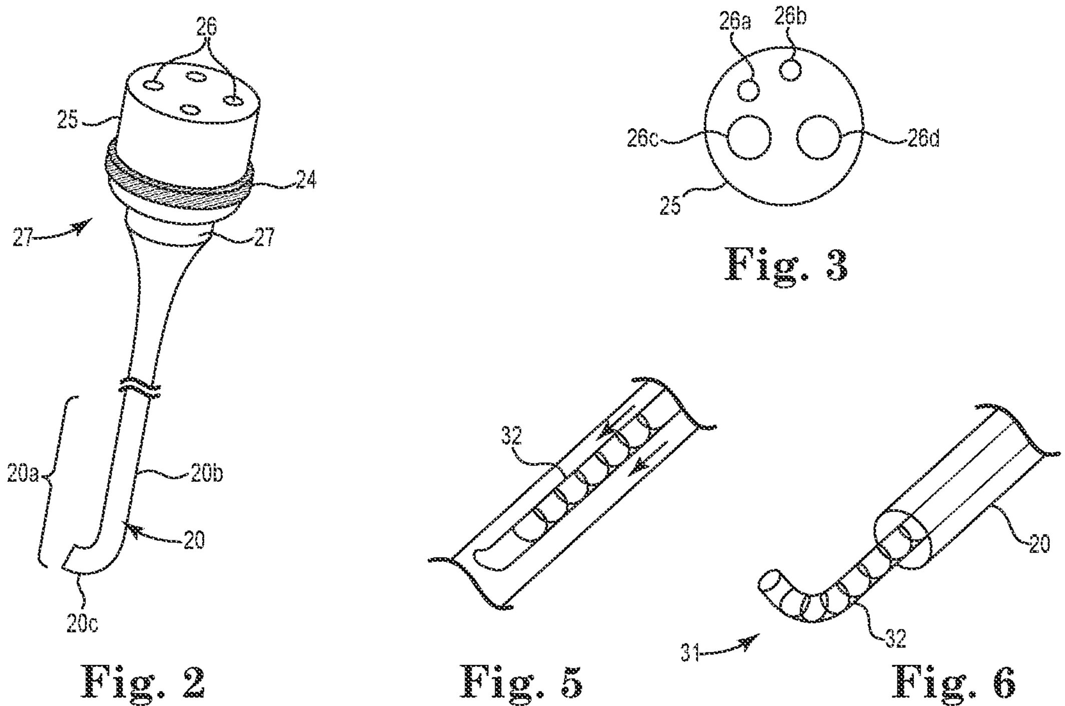
FIGS. 2 through 4 illustrate various embodiments of an introducer of the system of FIG. 1.
FIGS. 5 and 6 illustrate one embodiment of a catheter of the system of FIG. 1.
Figure 4:
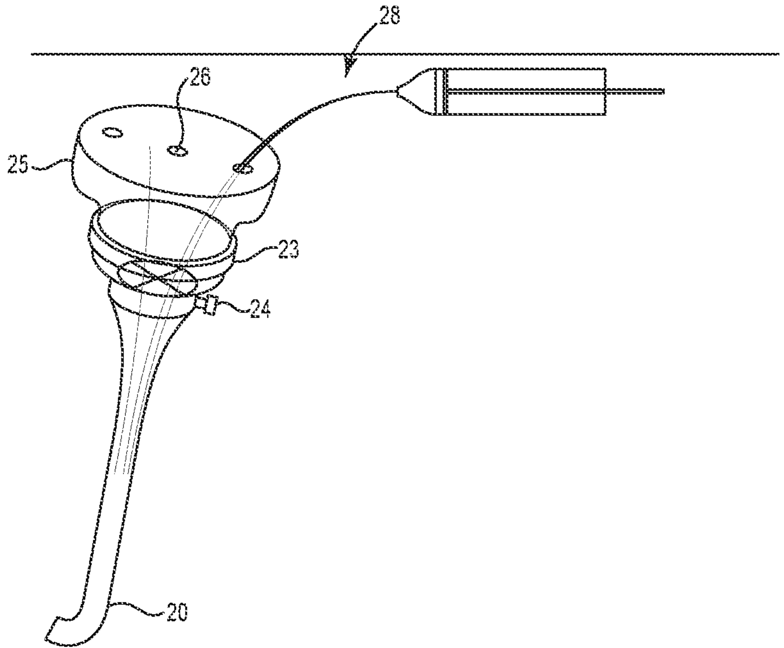

FIGS. 2-4 depict various aspects of the curved introducer sheath 20 with an optional multi-port introducer 25. As can be understood from FIG. 2, the curved introducer sheath 20 has dimensions and orientation which align with the CSF space, which can be difficult to navigate. In one embodiment, the sheath 20 is made of a polyurethane jacket over a metal or metal alloy core. The metal core may be a flexible nitinol alloy, to maintain the slight bend during introduction and navigation, and retain that slight bend despite repeated use. In certain embodiments, the curved introducer sheath 20 may be configured to have a bend radius of between approximately 2 mm and approximately 7 mm. The jacket may be of a braided construction embedded within silicone, nylon, or polyurethane. The use of a nitinol core enables the distal end of the sheath 20 to be more "spring-like" and move back to its original shape when it is delivered through a hollow tube (e.g., a Tuohy needle). In one embodiment, the sheath 20 has a generally hydrophilic distal section 20*a* to facilitate smooth placement of the catheter into the lumbar region (e.g., L3/L4). The sheath helps prevent tracking of blood and tissue into the spinal canal, to reduce the incidence of blockages when the therapy begins. The sheath 20 may further enable a 5 F or 6 F catheter having a length of approximately 7 cm to approximately 11 cm to be placed above or below the spinal cord. The distal section includes a shaft region 20*b* and generally curved tip 20*c*, which may crescent shaped or similar to the shape of a hockey stick. The distal section 20*a* is between approximately 10 cm to approximately 15 cm in length and the tip 20*c* is approximately 2-4 cm in length. The angle between the shaft region 20*b* and the tip 20*c* is approximately 120 degrees. In certain embodiments a catheter may comprise regions or portions having different thicknesses, diameters, materials, coils, coil pitches, and other features and designs to facilitate a particular bend radius and/or optimal pushability without compromising safety.

In use, the introducer sheath 20 may be inserted through or over a needle (not shown), such as a Tuohy needle, that has punctured the CSF space 15, for example, the cervical or lumbar area of the spine. The needle may be removed, leaving the introducer sheath 20 behind. The introducer sheath 20 may be curved to guide instruments from outside the body into the CSF space via a multi-port introducer 25, for example.

Multi-Port Introducer

An introducer may be used at the proximal end 21 of the introducer sheath 20. Any suitable introducer may be used, as desired, including a single-port introducer. As shown in FIGS. 2-4, in one embodiment, a multi-port introducer 25 may be attached or coupled to the proximal end 21 of the introducer sheath 20, for example by a connector 23. The connector 23 may be a Luer-Lock fitting, such as the Luer-Lok manufactured by Becton, Dickinson and Company. The multi-port introducer 25 includes a plurality of ports or openings 26 and a knob 24 or other structure to help with the steerability of the introducer. The knob may be associated with a valve, and/or it may help indicate the orientation of the catheter based on where the location of the end of the curved sheath/catheter. That is, if the knob is on the same side of the catheter as the curved tip, then when the catheter is in situ, the user will know the orientation of the curved tip as indicated by the knob. The multi-port introducer 25 may be made of any suitable material, such as an injection-molded plastic. The connector 23 may be made of nylon, polypropylene, polycarbonate or PVDF, or other appropriate material. In one embodiment, the introducer/sheath/peelaway sheath is configured for a 6 F catheter and has a shaft length of about 7 cm to about 11 cm and the guidewire is about 120 cm to about 180 cm in length which equates to the length of the catheter outside the body, which is from approximately 80 cm to approximately 130 cm, plus approximately 40 cm to approximately 60 cm, which is approximately the length of the catheter in the spine.

The introducer 25 may include any suitable number of ports. In one embodiment, the introducer 25 includes four ports 26. In other embodiments, the introducer 25 includes one port, two ports, three ports, five ports, six ports or more. Each port 26 includes a valve 27 or other structure to prevent backflow or fluid from leaking from the CSF space and out through the port 26. In one embodiment, the valve 27 is a check valve, a one-way valve, or non-return valve. The valve 27 may be adapted such that a catheter or other device may be introduced through the valve 27 without allowing fluid within the lumen of introducer sheath 20 to escape, and, conversely, without allowing foreign substances to enter the lumen of introducer sheath 20. In certain implementations, the ports 26 and valves 27 may be used to sample fluid at multiple time points and/or for checking flow/pressure.

The multi-port introducer 25 may be a manifold or entry point for catheters, endoscopes, guidewires, flush tubes, and/or other medical instruments, and the sheath 20 may include a lumen for passing any of these. Each port may have the same or similar diameter or may have different diameters. In one embodiment, as shown in FIG. 3, a four port introducer 25 includes two small diameter ports 26*a*, 26*b* and two larger diameter ports 26*c*, 26*d*. The two smaller diameter ports 26*a*, 26*b* may have a diameter of approximately 0.3 mm to approximately 1 mm and are configured to receive a medical instrument 28, such as a pressure transducer and/or flow transducer or sensors or other smaller diameter instrument. The two larger diameter ports 26*c*, 26*d* may have a diameter of approximately 1 mm to approximately 3 mm and are configured to receive a medical instrument 28, such as a flow catheter or other larger diameter instrument. In certain implementations, the introducer 25 may have a radiused or otherwise tapered design configured to maintain a good seal with the catheter to prevent or substantially resist accumulation of debris as well as fluid leakage back from the catheter.

In use, the surgeon can attach the multi-port introducer device 25 to the proximal end 21 of the introducer sheath 20 or the device 25 may already be attached prior to use. The surgeon can then use the various ports 26 to insert and/or remove different medical instruments 28, such as guidewires, cauterizers, micro-manipulators, sensors, etc. through the introducer sheath 20 and into a catheter in the CSF space for a procedure. Advantageously, the instruments 28 are aligned with the CSF space in the spinal column after introduction through the introducer sheath 20.

Catheter

As indicated in FIGS. 5-27, and with reference to FIG. 1, the system 5 may further include a curved catheter 30. In some embodiments, the catheter 30 may include a shielded coating for MRI-safety and to provide little to no reduction in image quality with specific scans such as gradient echo scans or fast spin scans. In some embodiments, the catheter 30 is a 5 F catheter. In some embodiments, the catheter 30 is a 6 F catheter with an approximately 7-10 cm introducer. In some embodiments, as shown in FIGS. 5 and 6, the tip 31 of catheter 30 may be spring-loaded, such that the catheter 30 maintains a generally linear form during delivery through the introducer 20 but transitions into a curved shape as it exits the introducer sheath 20 or needle. In one embodiment, the tip 31 is a curved atraumatic spring-loaded tip. The spring 32 may be made of a shape memory material, such as nitinol, or metal, such as stainless steel, or a metal alloy. In other embodiments, coil, braid, mesh, or other materials can be used in addition to or in lieu of a spring. The spring loaded tip 31 has a curved shape with a curve or bend of less than or equal to about 90 degrees. As explained above with respect to the curved introducer sheath, the curve or bend in the catheter tip facilitates a smooth transition from the outside of the body in the L5 region through to the spinal canal. In addition, it helps to avoid nerve roots in this region and help align the distal tip for its movement up to the cervical region. The curve or angle provides access to the CSF space on a patient that is likely lying perpendicularly, but the catheter and wire make a bend to traverse the canal smoothly and with reduced or minimal kinking, pinching, and/or strain near the point of entry. Sharp bends of 90 degrees or less can reduce flow of CSF through the catheter and facilitate clotting via the formation of stagnant flow and local eddy currents, which can block holes and result in therapy failure. In certain embodiments, the bend radius may be between approximately 0 mm and approximately 10 mm. In certain implementations, this bend radius may enable optimal CSF flow through a luminal device in the spinal canal.

In some embodiments, the bend radius may be between approximately 3 mm and approximately 7 mm. In certain embodiments, the catheter may comprise a coiled wire having a coil pitch selected to provide particular rigidity for navigation and for unblocking the catheter For example, in certain implementations, the coil pitch may be between approximately 0.01 inches and approximately 0.03 inches. In some embodiments, the catheter 30 is a lumbar catheter and is configured for delivery in a lumbar region of the spinal column. In some embodiments, the catheter 30 is a cervical catheter and is configured for delivery in a cervical region of the spinal column. While certain embodiments of the introducer, introducer sheath, catheter and other components of the present invention may be described as having a curve, bend radius, or a radius of curvature, it is to be understood that some or all of the components of the present invention may be provided straight, i.e., with no curve.

In use, once the introducer sheath 20 is in place in the patient, a catheter 30 (or other instruments) can be introduced through the introducer into the CSF space. Advantageously, the catheter 30 is aligned with the CSF space in the spinal column after introduction through the introducer sheath 20. In some embodiments, the catheter is navigated up to the cervical region in the C-2 area, or higher into the ventricles, to facilitate the drainage of fluids.

As illustrated in FIGS. 7-27, the catheter 30 may include structures that assist in the access to and/or navigation of the CSF space, and that facilitate the efficacy of the neuropheresis. Some of these structures include, but are not limited to, temperature, pressure, flow, and/or other sensors or transducers 40 (see, e.g., FIG. 1); structures to provide strain relief and/or kink resistance to the catheter (see, e.g., FIGS. 7-9, among others); visualization features (see, e.g., FIGS. 10-27); structures to increase flow profile (see, e.g., FIGS. 10-27); structures to unblock and/or catch blood clots, to reduce filter clogging (see, e.g., FIGS. 28-33); structures to help position or advance the catheter within the CSF space (see, e.g., FIGS. 1 and 11); and structures to allow multiple instruments to be introduced into the CSF space simultaneously (see, e.g., FIGS. 39 through 52).

Sensors

As can be understood from FIG. 1, in some embodiments, transducers 40, such as sensors or microsensors 40, are positioned on or about the catheter 30 or other instrument or may be embedded within the catheter wall. The transducers 40 may include pressure sensors, flow sensors, temperature sensors and/or sensors designed to measure other parameters such as viscosity, turbidity, or the like associated with normal, disease, and/or injury states of the CSF space. The transducers 40 may be positioned along the length L of the catheter or at or near a distal end 33 of the catheter 30. The transducers 40 may be positioned at locations that correspond to specific lumbar or cervical regions of the spine and measure flow and pressure at those locations. The pressure and flow sensors may also be used for kink or clog detection, as described below.

Strain Relief and Kink Resistance

Figures 7, 8, 9:
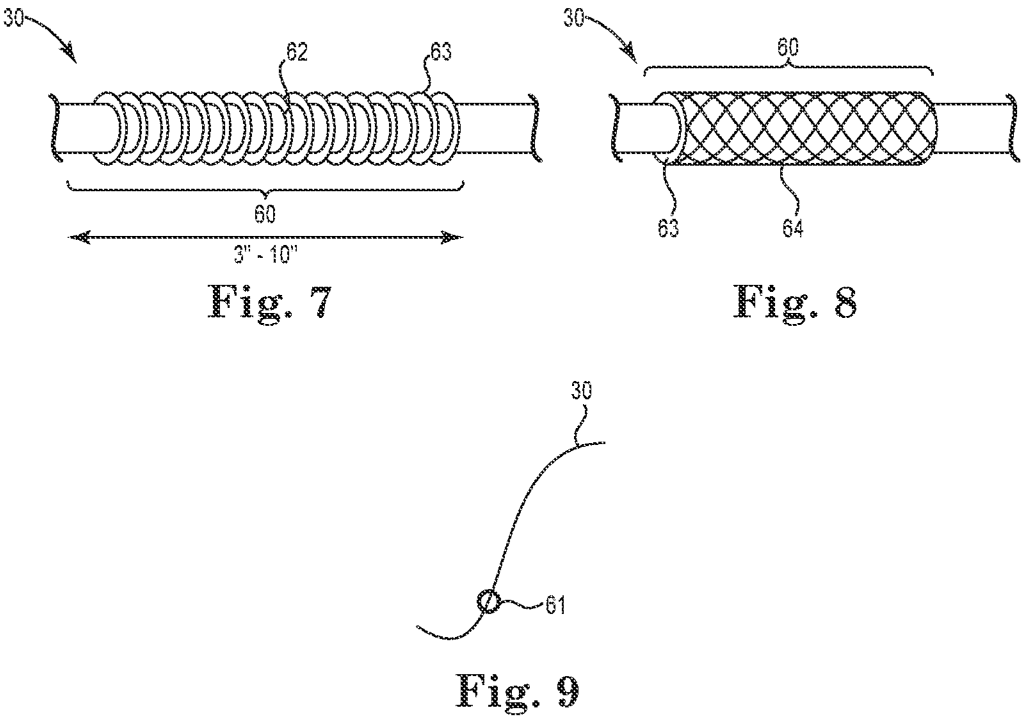
FIGS. 7 through 9 illustrate some embodiments of a catheter of the system of FIG. 1 having spring-loaded tips.

As indicated in FIGS. 7-9 and with reference to FIGS. 10-27, the catheter 30 may include a strain relief and kink resistance feature 60. The feature 60 may be a sleeve configured to be positioned over or about the catheter 30 at a desired location and may be "locked" in position (e.g., passive fixation) for a period of time, such as between about 30 minutes and about 120 minutes. For example, such a feature 60 may be provided at a fracture point 61 of the body of the catheter 30 for strain relief and to allow flex or deformation of the catheter (see FIG. 9). As shown in FIG. 7, in one embodiment, the feature 60 is a coiled wire 62, which may be embedded in a flexible tube 63, such as a silicone or polyether block amide (e.g., as sold under the trade name PEBAX) tube 63.

In certain implementations, the coiled wire 62 may comprise an approximately 0.003" round wire. In certain implementations, the coiled wire 62 may be configured with a coil pitch of between approximately 0.01" and approximately 0.03", however other configurations are also possible. This arrangement may enable the catheter to make a bend into a spinal canal and retain its position without kinking or compromising flow and flow under suction. In some implementations, the pitch may change over the length of the catheter 30. For example, a distal section may have a coil pitch of between approximately 0.06" and approximately 0.07", while a proximal portion may have a coil pitch of between approximately 0.01" and approximately 0.03". In some implementations, the coil pitch may be between approximately 0.027" and approximately 0.037" in the proximal section. The coil pitch may be selected to enable the size of inlet or other holes in the catheter to fit within the coil spacing. The coil pitch may also be selected to enable a kink-resistant design while maintaining pushability.

In another embodiment, as shown in FIG. 8, the feature 60 may be a braided wire 64 embedded in a tube 63. In various embodiments, the feature 60 is between approximately 3 inches and approximately 10 inches in length. In some embodiments, the feature 60 is approximately 3 inches, approximately 4 inches, approximately 5 inches, approximately 6 inches, approximately 7 inches, approximately 8 inches, approximately 9 inches, approximately 10 inches in length, or any other desired dimension.

Figure 10:
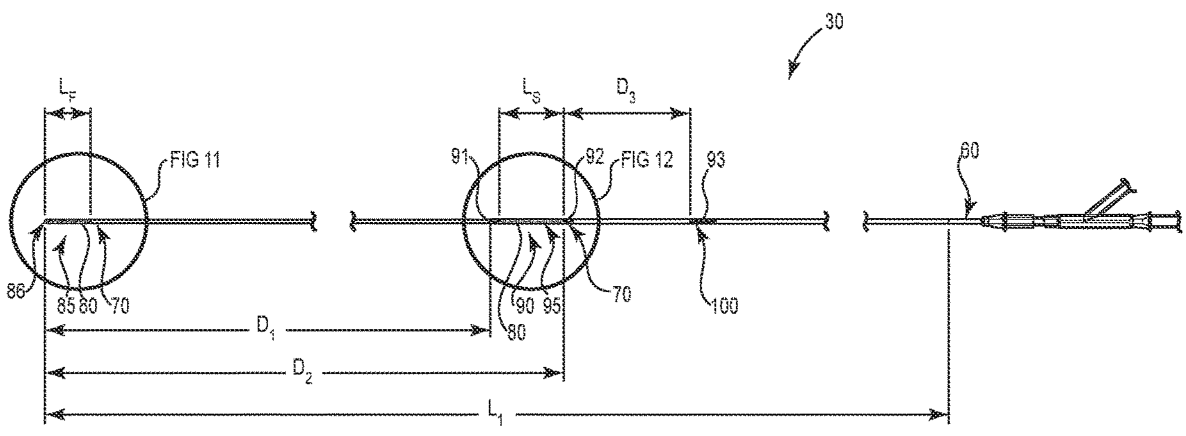
FIG. 10 illustrates an embodiment of a catheter of the system of FIG. 1.

As can be seen in FIG. 10 and others, a position marker 100, such as a green polyether block amide (e.g., PEBAX) position marker 100, may be integral with the catheter, or it may be positioned about or around the catheter. The position marker 100 is provided to indicate a transition point of the catheter at a point where it is entering/exiting the body. Such an indicator may be useful if imaging technology (e.g., MRI) is not used and the indicator can provide a guide. The position marker 100 also provides additional strength and kink resistance.

Visualization Features

In some embodiments, as shown in FIGS. 10-27, the catheter 30 may include a visualization feature 70 for diagnostic imaging purposes. The visualization feature 70 may be a marker band 70 that will help to confirm the location of the inlet and outlet at, for example, the cisterns in the spine, rather than placing the catheter near nerve tissue, soft pia mater, or other tissue that can be drawn into the catheter, thereby reducing flow.

Increased Flow Profile

CSF flow through the spinal column is considered a generally low flow system, as compared to a higher flow system such as the cardiac system. As can be understood from FIGS. 10-27, to increase the CSF or other fluid flow profile through the system 5, the catheter 30 optionally may include a plurality of openings 80 (which may or may not have a defined pattern) along certain portions of the catheter 30. The openings 80 may be elongated openings defined within the outer circumferential wall 30*a* of the catheter 30 and may be of oval, elliptical, other, or undefined shape. In some embodiments, the plurality of openings 80 has a total cross sectional surface area of approximately 0.6 $mm^2$ or greater, or approximately 1.5 $mm^2$. In general, the ratio of the cross sectional area of the openings 80 to the cross sectional area of an internal lumen of the catheter 30 is from 1:1 to 3:1. In one embodiment, the plurality of openings 80 has a total cross sectional surface area of approximately 0.8 $mm^2$. The openings 80 (which may be vents, slots, slits, or other) in the catheter 30 provide an increased flow profile for the system 5.

Figure 11:
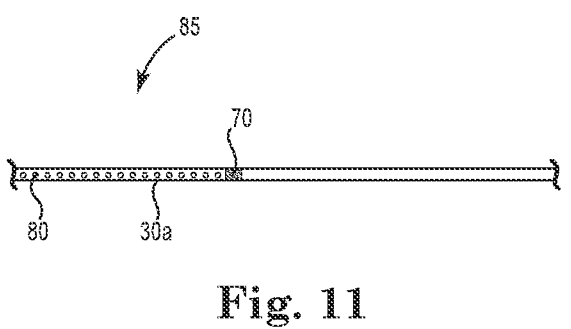
FIG. 11 illustrates a first, distal portion of the catheter of FIG. 10.
Figure 12:
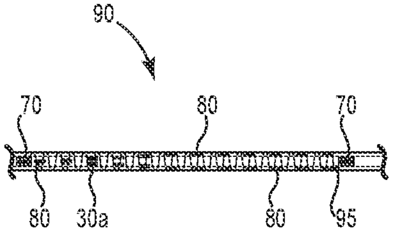
FIG. 12 illustrates a second, medial portion of the catheter of FIG. 10.

As shown in FIGS. 11 and 12, and with reference to FIG. 10, in one embodiment, a first portion 85 of catheter 30 may optionally include a plurality of openings 80 positioned generally linearly along or generally parallel to or along a horizontal line through a lumen of the catheter 30. The distal end 86 of the first portion 85 may optional includes a round or rounded tip, or a soft distal portion, to prevent puncture or lessen damage to any nearby tissue or other anatomical feature during delivery of the device. The length LF of the first portion 85 is approximately 2 cm. A second portion 90 of catheter 30 includes a plurality of openings 80, which may be positioned in a random, staggered, symmetrical, or other pattern (or non-pattern) relative to a horizontal line defined through a lumen of the catheter 30. The second portion 90 also optionally may include a spring or coil 95, which may be provided for reinforcement of the inner and outer lumens. The function of the spring 95 is to lessen the likelihood of collapse of the section, from suction or from the weight of tissue on the catheter or otherwise. The coil or spring 95 may be made of platinum, stainless steel, or other suitable materials depending on whether imaging is desired. Any suitable number of springs or coils may be used. The length $L_S$ of the second portion 90 is approximately 3 cm. The distance $D_1$ between a distal end 86 of the first portion 85 and a distal end 91 of the second portion 90 is approximately 30 cm. The distance $D_2$ between a distal end 86 of the first portion 85 and a proximal end 92 of the second portion 90 is approximately 33 cm. In some embodiments, the distance $D_2$ between a distal end 86 of the first portion 85 and a proximal end 92 of the second portion 90 is between approximately 33 cm and approximately 38 cm. The total length $L_1$ of the catheter 30 is approximately 68 cm. The distance $D_3$ between the proximal end 92 of the second portion 90 and a distal end 93 of the position marker 100 is approximately 6 cm.

Figure 13:
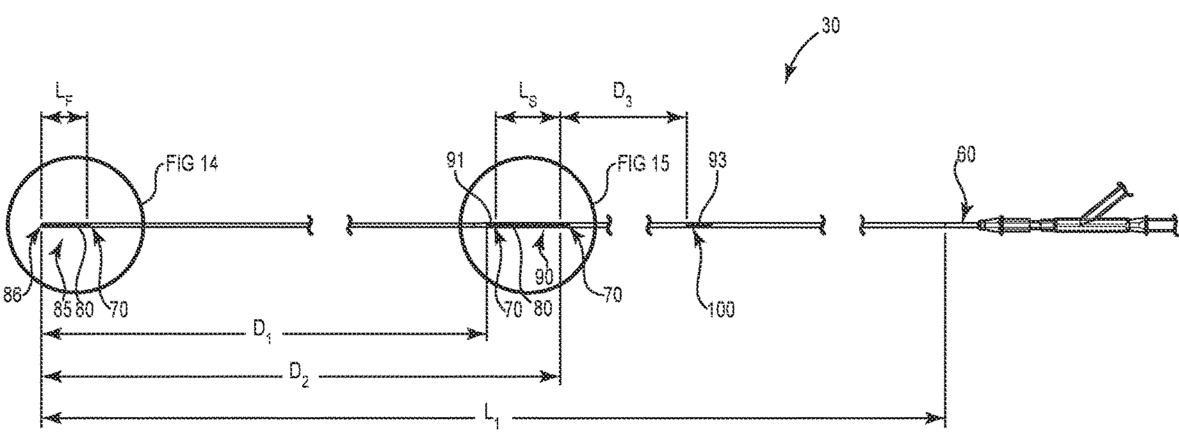
FIG. 13 illustrates an embodiment of a catheter of the system of FIG. 1.
Figures 14, 15:
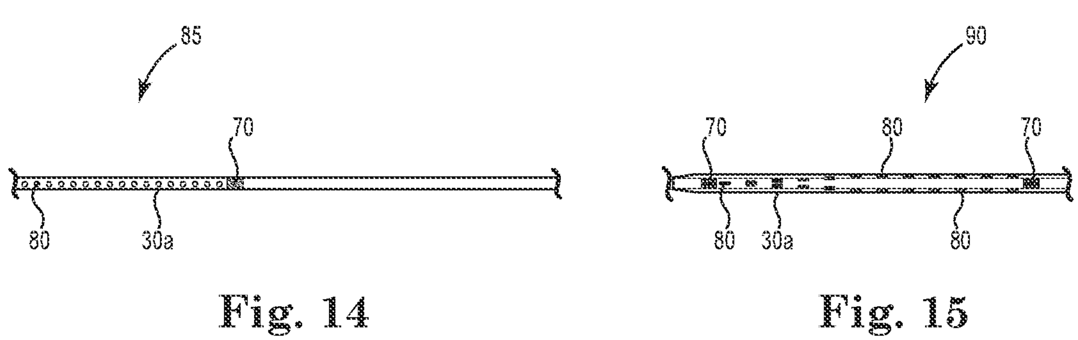
FIG. 14 illustrates a first, distal portion of the catheter of FIG. 13.
FIG. 15 illustrates a second, medial portion of the catheter of FIG. 13.

As shown in FIGS. 14 and 15, and with reference to FIG. 13, in one embodiment, a first portion 85 of catheter 30 may optionally include a plurality of openings 80 positioned generally linearly along or generally parallel to or along a horizontal line through a lumen of the catheter 30. The distal end 86 of the first portion 85 may include a round or rounded tip or a soft distal end portion to prevent puncture or lessen damage to any nearby tissue or other anatomical feature during delivery of the device. The length LF of the first portion 85 is approximately 2 cm. A second portion 90 of catheter 30 includes a plurality of openings 80, which may be positioned in a random, staggered, symmetrical, or other pattern relative to the horizontal line through a lumen of the catheter 30. The length $L_S$ of the second portion 90 is approximately 3 cm. The distance $D_1$ between a distal end 86 of the first portion 85 and a distal end 91 of the second portion 90 is approximately 20 cm. The distance $D_2$ between a distal end 86 of the first portion 85 and a proximal end 92 of the second portion 90 is approximately 23 cm. The total length $L_1$ of the catheter 30 is approximately 58 cm. The distance $D_3$ between the proximal end 92 of the second portion 90 and a distal end 93 of the position marker 100 is approximately 6 cm.

Figure 16:
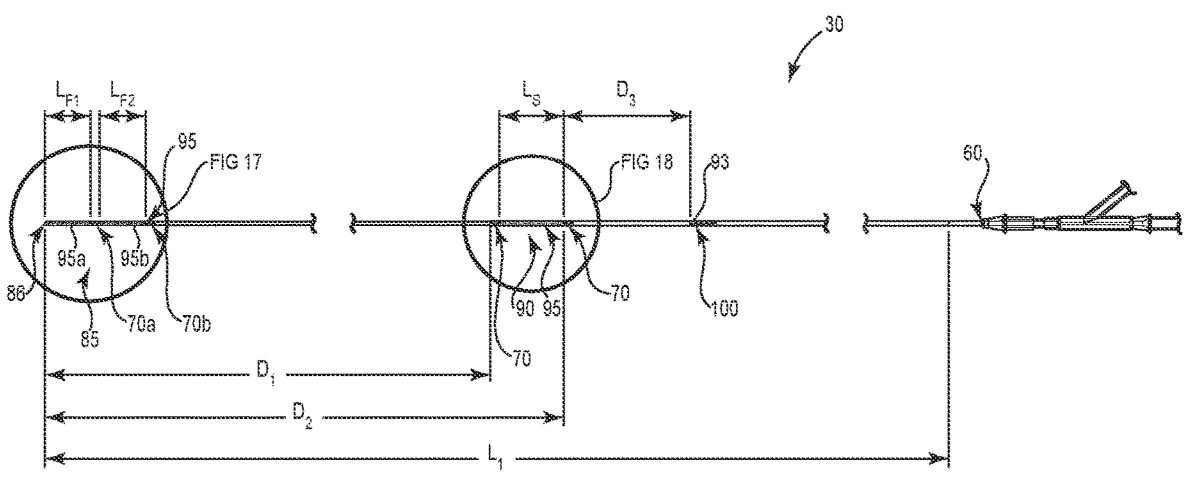
FIG. 16 illustrates an embodiment of a catheter of the system of FIG. 1.
Figures 17, 18:
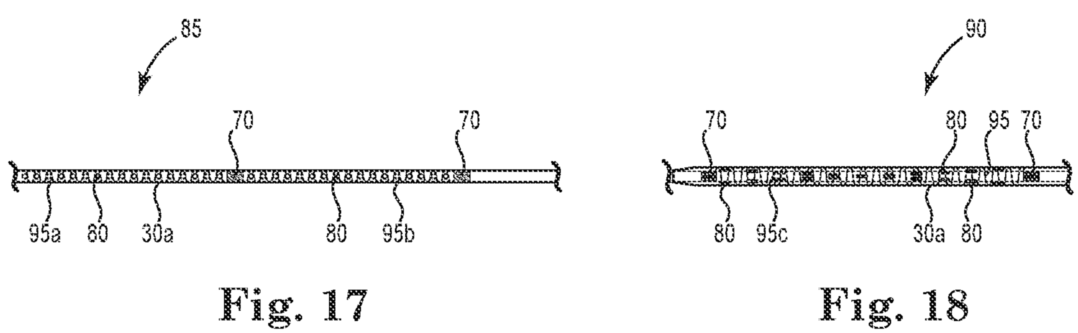
FIG. 17 illustrates a first, distal portion of the catheter of FIG. 16.
FIG. 18 illustrates a second, medial portion of catheter of FIG. 16.

As shown in FIGS. 17 and 18, and with reference to FIG. 16, in one embodiment, a first portion 85 of catheter 30 may optionally include a plurality of openings 80 positioned generally linearly along or generally parallel to a horizontal line through a lumen of the catheter 30. The distal end 86 of the first portion 85 may include a round or rounded tip or a soft distal end portion to prevent puncture or lessen damage to any nearby tissue or other anatomical feature during delivery of the device. The first portion 85 also may include springs or coils 95*a*, 95*b* separated by a marker band 70. The springs or coils 95 resist reinforcement of the inner and outer lumens. The separation of the springs 95*a*, 95*b* resists collapse of the section from suction or from the weight of tissue on the catheter. The coils or springs 95 may be made of platinum or stainless steel depending on whether imaging is desired. Any suitable number of springs or coils may be used, with or without one or more marker bands. The length $L_{F1}$ of the first portion 85 between the distal end 86 and the marker band 70*a* is approximately 2 cm. The length $L_{F2}$ of the first portion 85 between the marker band 70*a* and marker band 70*b* is approximately 2 cm. A second portion 90 of catheter 30 may include a plurality of openings 80 positioned in a random, staggered, symmetrical, or other pattern relative to a horizontal line through a lumen of the catheter 30. The second portion 90 also may include a spring 95*c*. The separation of the springs 95*a*, 95*b* and 95*c* resists collapse of the section from suction or from the weight of tissue on the catheter. The length $L_S$ of the second portion 90 is approximately 3 cm. The distance $D_1$ between a distal end 86 of the first portion 85 and a distal end 91 of the second portion 90 is approximately 30 cm. The distance $D_2$ between a distal end 86 of the first portion 85 and a proximal end 92 of the second portion 90 is approximately 33 cm. In some embodiments, the distance $D_2$ between a distal end 86 of the first portion 85 and a proximal end 92 of the second portion 90 is between approximately 33 cm and approximately 38 cm. The total length $L_1$ of the catheter 30 is approximately 68 cm. The distance $D_3$ between the proximal end 92 of the second portion 90 and a distal end 93 of the position marker 100 is approximately 6 cm.

Figure 19:
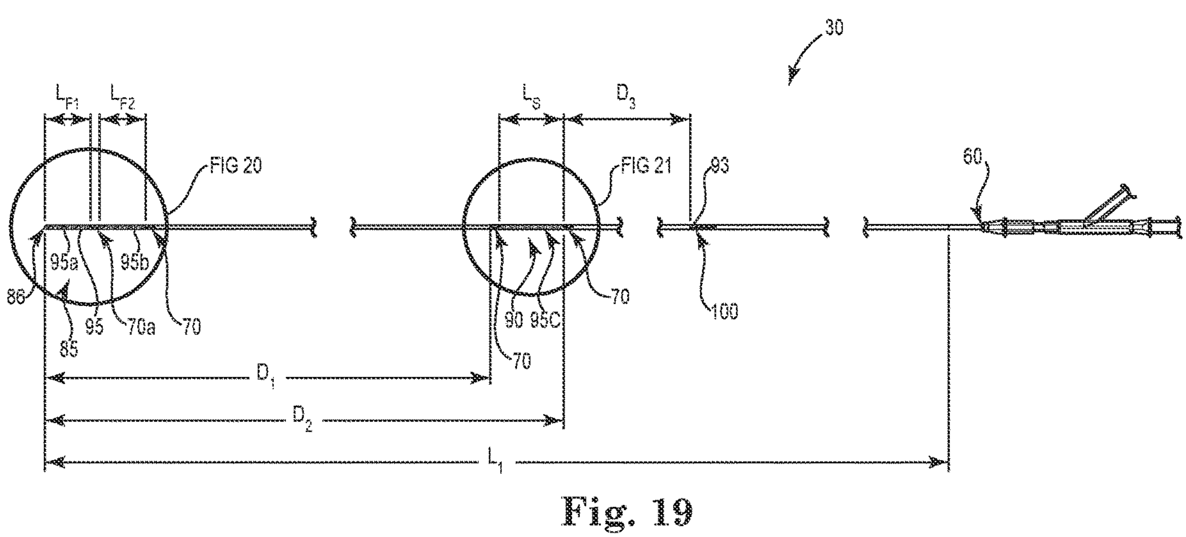
FIG. 19 illustrates an embodiment of a catheter of the system of FIG. 1.
Figure 20:
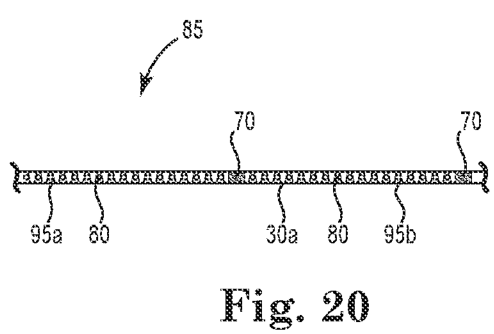
FIG. 20 illustrates a first, distal portion of the catheter of FIG. 19.
Figure 21:
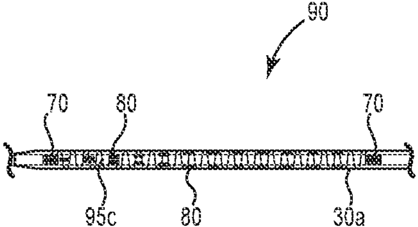
FIG. 21 illustrates a second, medial portion of the catheter of FIG. 19.

As shown in FIGS. 20 and 21, and with reference to FIG. 19, in one embodiment, a first portion 85 of catheter 30 includes a plurality of openings 80 positioned generally linearly along or generally parallel to a horizontal line through a central lumen of the catheter 30. The distal end 86 of the first portion 85 may include a round or rounded tip or soft distal end portion to prevent puncture or lessen damage to any nearby tissue or other anatomical feature during delivery of the device. The first portion 85 also may include springs 95*a*, 95*b* separated by a marker band 70. The springs or coils 95 resist reinforcement of the inner and outer lumens. The coils or springs 95 may be made of platinum, stainless steel, or other suitable materials depending on whether imaging is desired. The separation of the springs 95*a*, 95*b* resists collapse of the section from suction or from the weight of tissue on the catheter. The coils or springs 95 may be made of platinum, stainless steel, or other suitable materials depending on whether imaging is desired. Any suitable number of springs or coils may be used. The length $L_{F1}$ of the first portion 85 between the distal end 86 and the marker band 70*a* is approximately 2 cm. The length $L_{F2}$ of the first portion 85 between the marker band 70*a* and marker band 70*b* is approximately 2 cm. A second portion 90 of catheter 30 may include a plurality of openings 80 positioned in a random, staggered, symmetrical or other pattern relative to a horizontal line through a lumen of the catheter 30. The second portion 90 also includes a spring 95*c*. The separation of the springs 95*a*, 95*b* and 95*c* resists collapse of the section from suction or from the weight of tissue on the catheter. The length $L_S$ of the second portion 90 is approximately 3 cm. The distance $D_1$ between a distal end 86 of the first portion 85 and a distal end 91 of the second portion 90 is approximately 20 cm. The distance $D_2$ between a distal end 86 of the first portion 85 and a proximal end 92 of the second portion 90 is approximately 23 cm. The total length $L_1$ of the catheter 30 is approximately 58 cm. The distance $D_3$ between the proximal end 92 of the second portion 90 and a distal end 93 of the position marker 100 is approximately 6 cm.

Figure 22:
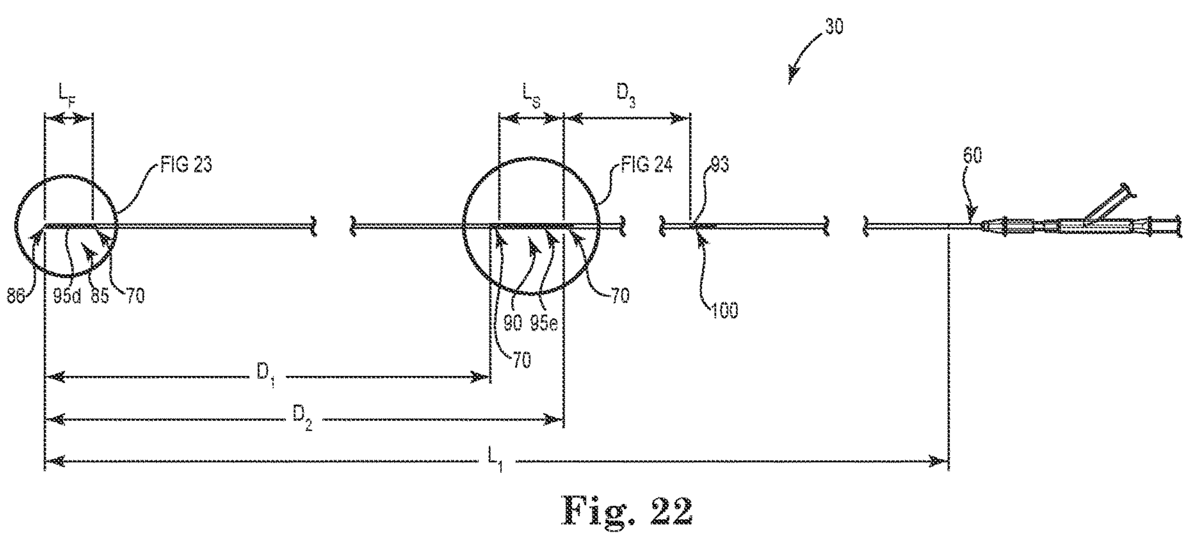
FIG. 22 illustrates an embodiment of a catheter of the system of FIG. 1.
Figures 23, 24:
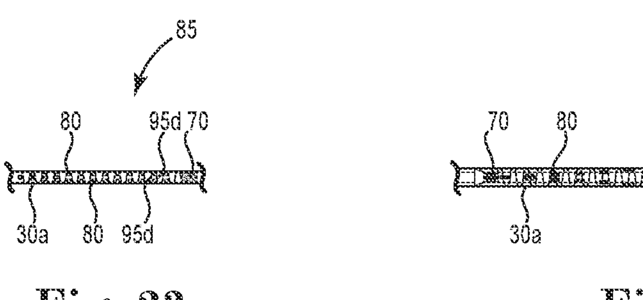
FIG. 23 illustrates a first, distal portion of the catheter of FIG. 22.
FIG. 24 illustrates a second, medial portion of the catheter of FIG. 22.

As shown in FIGS. 23 and 24, and with reference to FIG. 22, in one embodiment, a first portion 85 of catheter 30 includes a plurality of openings 80 positioned in a random, staggered, symmetrical or other pattern relative to a horizontal line through a lumen of the catheter 30. The distal end 86 of the first portion 85 may include a round or rounded tip or a soft distal end portion to prevent puncture or lessen damage to any nearby tissue or other anatomical feature during delivery of the device. The first portion 85 may also include a spring 95*d*. The spring or coil 95 resists reinforcement of the inner and outer lumens. The coil or spring 95 may be made of platinum, stainless steel, or other suitable materials depending on whether imaging is desired. Any suitable number of springs or coils may be use. The length LF of the first portion 85 is approximately 2.1 cm. A second portion 90 of catheter 30 may include a plurality of openings 80 positioned in a random, staggered, symmetrical or other pattern relative to a horizontal line defined through a lumen of the catheter 30. The second portion 90 also includes a spring 95*e*. The separation of the springs 95*d* and 95*e* resists collapse of the section from suction or from the weight of tissue on the catheter. The length $L_S$ of the second portion 90 is approximately 3 cm. The distance $D_1$ between a distal end 86 of the first portion 85 and a distal end 91 of the second portion 90 is approximately 30 cm. The distance $D_2$ between a distal end 86 of the first portion 85 and a proximal end 92 of the second portion 90 is approximately 33 cm. In some embodiments, the distance $D_2$ between a distal end 86 of the first portion 85 and a proximal end 92 of the second portion 90 is between approximately 33 cm and approximately 38 cm. The total length $L_1$ of the catheter 30 is approximately 68 cm. The distance $D_3$ between the proximal end 92 of the second portion 90 and a distal end 93 of the position marker 100 is approximately 6 cm.

Figure 25:
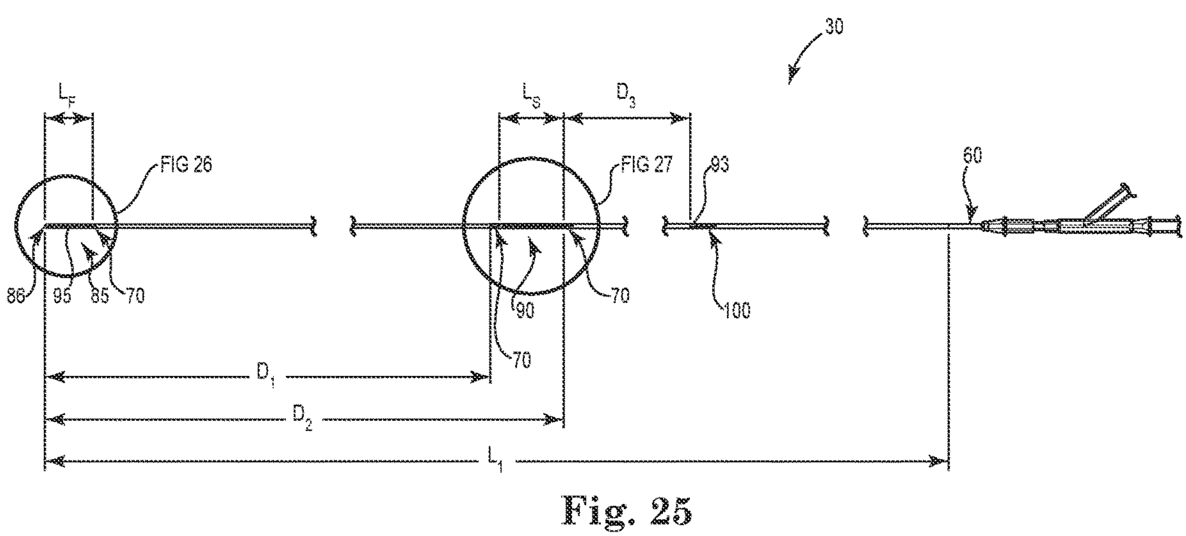
FIG. 25 illustrates an embodiment of a catheter of the system of FIG. 1.
Figure 26:
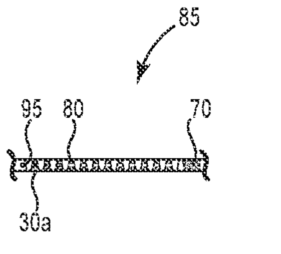
FIG. 26 illustrates a first, distal portion of the catheter of FIG. 25.
Figure 27:
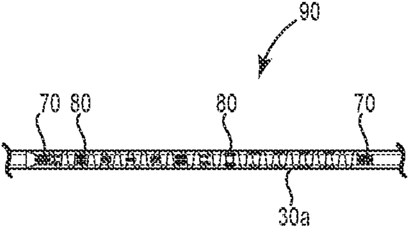
FIG. 27 illustrates a second, medial portion of the catheter of FIG. 25.

As shown in FIGS. 26 and 27, and with reference to FIG. 25, in one embodiment, a first portion 85 of catheter 30 includes a plurality of openings 80 positioned in a random, staggered, symmetrical or other pattern relative to a horizontal line through a lumen of the catheter 30. The distal end 86 of the first portion 85 includes a round or rounded tip or soft distal end portion to prevent puncture or lessen damage to any nearby tissue or other anatomical feature during delivery of the device. The first portion 85 may include a spring 95. The spring or coil 95 resists reinforcement of the inner and outer lumens. The coil or spring 95 may be made of platinum or stainless steel depending on whether imaging is desired. Any suitable number of springs or coils may be use. The length LF of the first portion 85 is approximately 2.1 cm. A second portion 90 of catheter 30 may include a plurality of openings 80 positioned in a random, staggered, symmetrical or other pattern relative to the horizontal line through a lumen of the catheter 30. The length $L_S$ of the second portion 90 is approximately 3 cm. The distance $D_1$ between a distal end 86 of the first portion 85 and a distal end 91 of the second portion 90 is approximately 20 cm. The distance $D_2$ between a distal end 86 of the first portion 85 and a proximal end 92 of the second portion 90 is approximately 23 cm. The total length $L_1$ of the catheter 30 is approximately 58 cm. The distance $D_3$ between the proximal end 92 of the second portion 90 and a distal end 93 of the position marker 100 is approximately 6 cm.

Blood Clot Removal

In some embodiments, the system 5 or catheter 30 may be used with other devices to help increase the efficiency and safety of the neuropheresis system. For example, blood clots can reduce or stop fluid flow in the vasculature and can cause similar problems in the CSF space. As such, their removal is desirable and can be accomplished with aspects of the systems and devices disclosed herein. In some embodiments, a chemical agent, such as saline, tissue plasminogen activator (tPA), or urokinase, may be introduced into the CSF space through the catheter 30 to unblock clots. To retrieve those clots, the system 5 may further include a basket, coiled wire, or other receptacle 105 to hold or remove pieces of the clot to reduce or prevent clogging of a filter.

Figures 28, 29, 30, 31, 32:
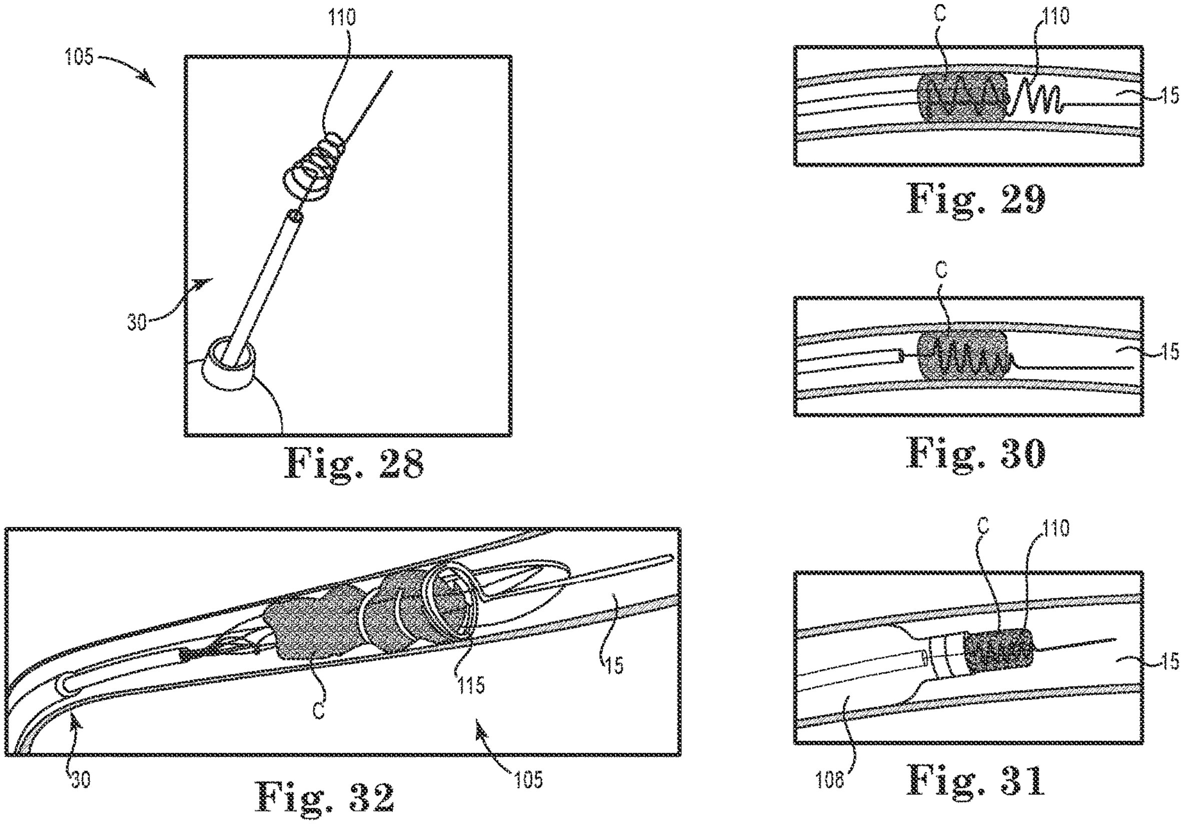
FIGS. 28 through 31 illustrate several embodiments of a blood clot removal device of the system of FIG. 1 having a coiled microwire.
FIG. 32 illustrates an embodiment of a blood clot removal device of the system of FIG. 1 having a plurality of intertwined microwires.

As shown in FIGS. 28 through 31, the receptacle 105 may be a coiled microwire 110 that may be inserted into the catheter 30 and advanced to the blood clot C. A balloon 108 may be positioned over the catheter 30 to either push tissue away from the openings in the catheter and enable flow to occur more easily, or to actually perform the function of isolation while suction (via pump) and/or mechanical manipulation with the micro-wires is applied. The coiled microwire 110 engages blood clot C by intertwining with pieces of clot C (see FIGS. 29 and 30). The microwire 110 with clot C intertwined may be withdrawn through the catheter 30, thereby removing the clot C from the CSF space (FIG. 31).

As indicated in FIG. 32, in another embodiment, the receptacle 105 may include a plurality of intertwined microwires 115 that may be inserted into the catheter 30 and advanced to the blood clot C. The multiple microwires 115 engage blood clot C by intertwining with pieces of clot C. The microwires 115 with clot C intertwined therein may be withdrawn through the catheter 30, thereby removing the clot C from the CSF space.

Figure 33:
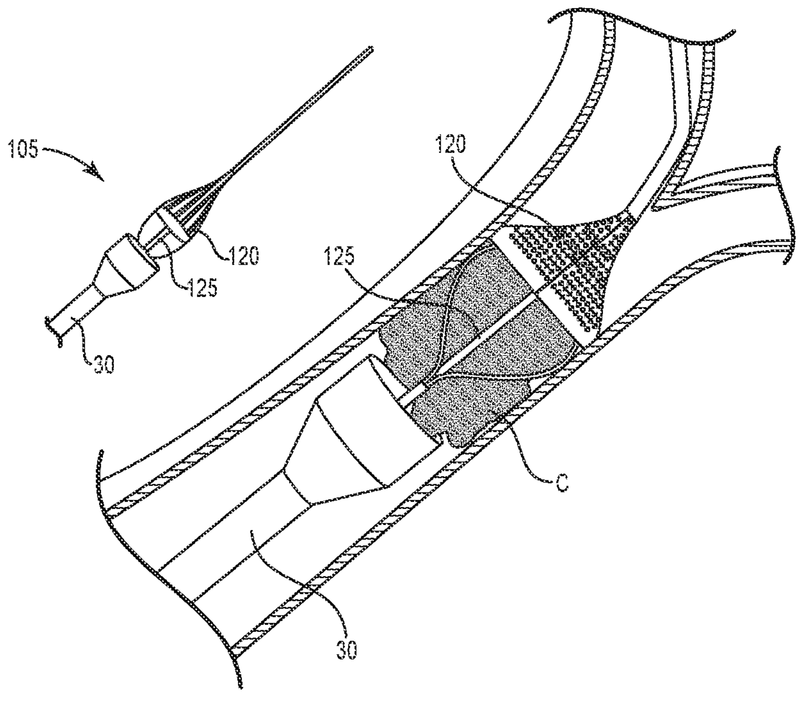
FIG. 33 illustrates an embodiment of a blood clot removal device of the system of FIG. 1 having a sieve mechanism.

As illustrated in FIG. 33, in another embodiment, the receptacle 105 may be a sieve mechanism 120 that may be attached to a microcatheter 125 that may be inserted into the catheter 30 and advanced to the blood clot C. A balloon 108 may be positioned over the catheter 30 as described above. The sieve mechanism 120 may include openings that are large enough to pass blood cells but small enough for the debris (clot C) to be captured by the sieve mechanism 120. As the mechanism 120 is withdrawn through the catheter 30, clot C is removed from the CSF space.

Figure 34:
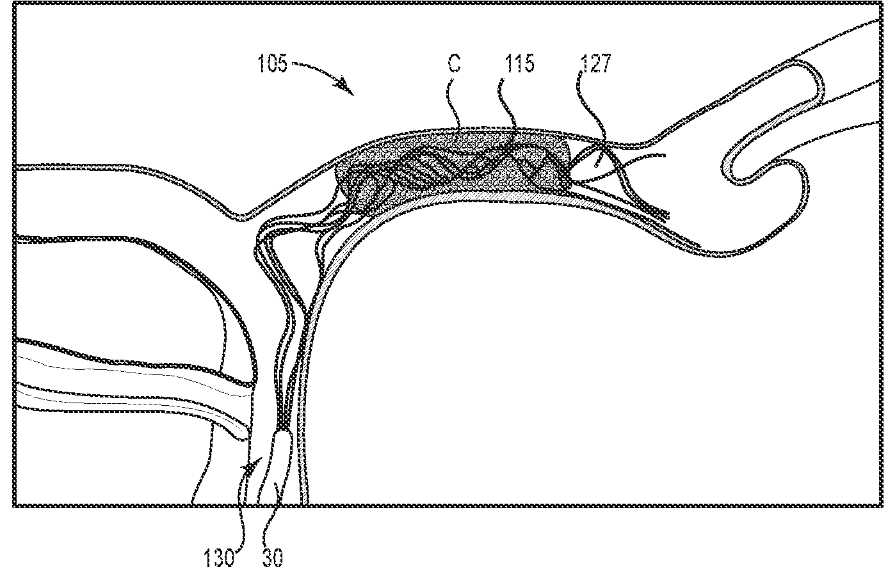
FIG. 34 illustrates an embodiment of a blood clot removal device of the system of FIG. 1 having a plurality of microwires.

As shown in FIG. 34, in another embodiment, the receptacle 105 may include a plurality of microwires 115, which may have pressure sensors 126 positioned on, in, or about the catheter 30. The pressure sensors 126 help detect problems in the overall flow circuit, and highlight when there is a blockage. A balloon (not shown) may be positioned over the catheter 30 as described above and the balloon may further be used to deploy flexible pressure sensors 127. In other embodiments, the flexible pressure sensors 127 may be printed on a substrate (e.g., silicone) and deployed at or near the blood clot C.

Balloons

As can be understood from FIGS. 35-38, in some embodiments, the system 5 or catheter 30 may be used with other devices to help increase the efficiency and safety of the neuropheresis system. For example, and as shown in FIGS. 35 and 36, in one embodiment, a positioning device 130 with multiple inflatable/deflatable balloons 135, each of which may have its own lumen and/or port 130*a*, can be inserted through the introducer sheath 20 (not shown) and directly into the spinal canal. The balloons 135 may be co-located with or disposed about the positioning device 130. In one embodiment, the balloon 135 has a length between approximately 0.5 cm and approximately 2.0 cm and a height between approximately 0.25 cm and approximately 0.6 cm. In some embodiments, the balloons 135 may be radiopaque to provide increased visualization of the catheter 30 or positioning device 130 within the CSF space.

As depicted in FIGS. 37 and 38, the positioning device's first (distal-most 135*a*) and second (next to first 135*b*) balloons may be inflated to push tissue structures back; the second balloon 135*b* can then be deflated, so that the catheter 30 can be advanced into the space that was occupied by tissue and nerves, before it was pushed back by the second balloon 135*b*. The first balloon 135*a* is deflated, and the deflated balloons are advanced further into the CSF space 15, where they are reinflated. This process is repeated until the catheter 30 is in the desired position in the spinal column, at which point the positioning device 130 can be withdrawn.

Multiple Lumens and Other Features of the Catheter

In some embodiments, the system 5 includes a multi-lumen (e.g. more than one lumen) catheter 30. A multi-lumen catheter can provide stability under a vacuum. The lumens themselves can provide redundancy such that, if one gets clogged, other lumens may be utilized. The lumens enable real-time sampling and spinal pressure measurement, thus enabling action to be taken if pressure is too high or too low which indicates blockage and/or overdrainage. In some embodiments, the diameter of the distal end is smaller (e.g., 4 French (4 F)) than the diameter of the proximal end in order to maintain flow despite the lack of space in the cervical region of the spine. In some embodiments, the diameter of the proximal end is greater than the diameter of the distal end to enable rapid drainage of large amounts of blood-filled CSF quickly. The catheters are constructed to maintain patency despite anatomical challenges, such as being squeezed by tissue in the dura or being subject to a large suction force from the pump on the walls of the catheter. In some embodiments, the catheter includes a cross sectional area of approximately 0.8 $mm^2$ to enhance flow and a round distal section to facilitate cervical placement via a guidewire. In some embodiments, the separation between the inlet and outlet is between approximately 33 cm and approximately 38 cm to reduce likelihood of local recirculating loops and enhance rapid clearing of a large amount, up to and including substantially all, of the entire volume of CSF.

In some embodiments, the inlet and outlet of the catheter are switched. For example, in a subarachnoid hemorrhage (SAH), there is often a bolus of bloody CSF at the base of the brain, which can leak into the spine over time. When the therapy is deployed and fluid is being moved at the rate of about 120/240 ml/hr (or any other desired rate), it may be helpful from time to time to switch the inlet and outlet of catheter (particularly if a short catheter is being used) to prevent local recirculation of fluid and enhance unfiltered CSF being drawn into the filter. Other therapeutic uses of switching the inlet and outlet includes use in a method of preventing stagnating flow, dislodging clots, and/or opening up blockages, which may be due to thick blood or suction effects on the inlet. In one embodiment, two microcatheters may be used within a central lumen to change the position of inlet and outlet. In other embodiments, an outer sheath with cut-outs or openings may be used to change the position of the inlet and outlet. Such a feature may also make clot-removal from within the catheter easier without having to extract the catheter and place it again.

In some embodiments, the catheter having a tubular body may include a plurality of openings over at least a portion of the tubular body. A sheath configured to cover certain openings on the tubular body may be used such that the catheter remains in place while the sheath is rotated to open or close the openings in the tubular body to increase or decrease flow as needed.

Figure 39:
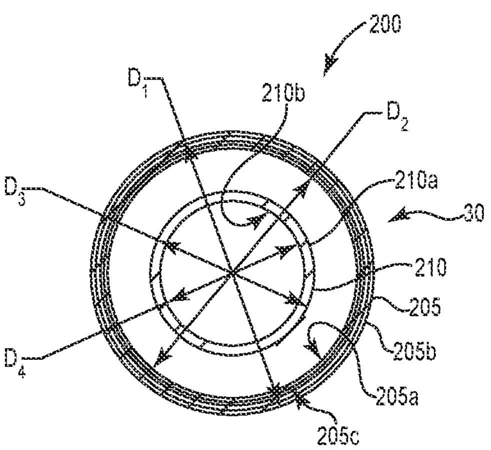
FIGS. 39 and 40 depict an embodiment of a dual lumen catheter having proximal and distal ends with varying diameters for use with the system of FIG. 1.
Figure 40:
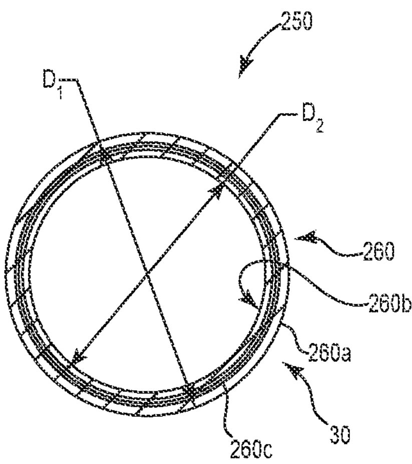

FIGS. 39 through 57 illustrate various embodiments of a catheter 30 that may be used with the present systems. FIGS. 39 through 42 illustrate embodiments of a catheter 30 having proximal and distal ends with varying diameters. More specifically, FIG. 39 and FIG. 40 illustrate one embodiment of a 5 F catheter 30 having a proximal end 200 with different dimensions than a distal end 250 of the catheter. As shown in FIG. 39, the proximal end 200 of the catheter 30 includes an outer lumen 205 and an inner lumen 210. The outer lumen 205 is defined by an inner wall 205*a*, and outer wall 205*b* and a middle wall 205*c*. Other embodiments may include greater or fewer walls. The outer wall 205*b* may be a 55D polyether block amide (e.g., a polyether block amide sold under name PEBAX) 5 F approximately 0.003" wall jacket. The outer wall 205*b* may have a diameter $D_1$ of about 0.065" or about 0.17 cm. The middle wall 205*c* may be about an approximately 0.001"×0.003" braid. The inner wall 205*a* may be a PTFE etching approximately 0.058" ID×0.0015" wall liner having a diameter $D_2$ of about 0.058" or about 0.15 cm. The inner lumen 210 is defined by an inner wall 210*b* and an outer wall 210*a*. The outer wall 210*a* may be a 55D polyether block amide 3 F approximately 0.003" wall having a diameter $D_3$ of about 0.038" or about 0.10 cm. The inner wall 210*b*.may have a diameter $D_4$ of about 0.033" or about 0.08 cm. As shown in FIG. 40, the distal end 250 of the catheter 30 includes an outer lumen 260 defined by an outer wall 260*a*, an inner wall 260*b*, and a middle wall 260*c*. Other embodiments may include greater or fewer walls. The outer wall 260*a* may be a 55D polyether block amide 4 F approximately 0.005" wall jacket having a diameter $D_1$ of about 0.054 in or about 0.14 cm. The middle wall 260*c* may be an approximately 0.001"×0.003" braid. The inner wall 260*b* may be a PTFE etched approximately 0.042"×0.0015" wall liner having a diameter $D_2$ of about 0.041" or about 0.10 cm.

Figure 41:
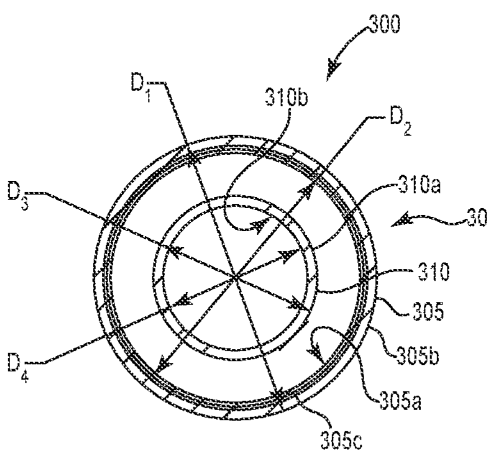
FIGS. 41 and 42 depict an embodiment of a dual lumen catheter having a proximal end with different dimensions than a distal end of the catheter for use with the system of FIG. 1.
Figure 42:
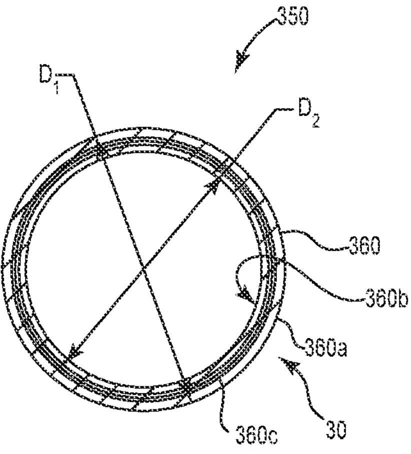

FIG. 41 and FIG. 42 illustrate one embodiment of a 6 F catheter 30 having a proximal end 300 with different dimensions than a distal end 350 of the catheter. As shown in FIG. 41, the proximal end 300 of the catheter 30 includes an outer lumen 305 and an inner lumen 310. The outer lumen 305 is defined by an inner wall 305*a*, an outer wall 305*b*, and a middle wall 305*c*. Other embodiments may include greater or fewer walls. The middle wall 305*c* may be an approximately 0.001"×0.003" braid. The outer wall 305*b* may be a 55D polyether block amide 6 F approximately 0.003" wall jacket. Any other suitable material and dimensions also may be used. The outer wall 305*b* may have a diameter $D_1$ of about 0.078" or about 0.20 cm. The inner wall 305*a* may be a PTFE etching approximately 0.068" ID×0.0015" wall liner having a diameter $D_2$ of approximately 0.068" or approximately 0.17 cm. The inner lumen 310 is defined by an inner wall 310*b* and an outer wall 310*a*. The outer wall 310*a* may be a 55D polyether block amide 3 F approximately 0.003" wall having a diameter $D_3$ of about 0.038" or about 0.10 cm. The inner wall 310*b* may have a diameter $D_4$ of about 0.033" or about 0.08 cm. As shown in FIG. 42, the distal end 350 of the catheter 30 includes an outer lumen 360 defined by an outer wall 360*a*, an inner wall 360*b*, and a middle wall 360*c*. Other embodiments may include greater or fewer walls. The outer wall 360*a* may be a 55D polyether block amide 4 F approximately 0.005" wall jacket having a diameter $D_1$ of about 0.054" or about 0.14 cm. The middle wall 360*c* may be an approximately 0.001"×0.003" braid. The inner wall 360*b* may be a PTFE etched approximately 0.042"×0.0015" wall liner having a diameter $D_2$ of about 0.041" or about 0.10 cm. Any other suitable material and dimensions also may be used.

Figure 43:
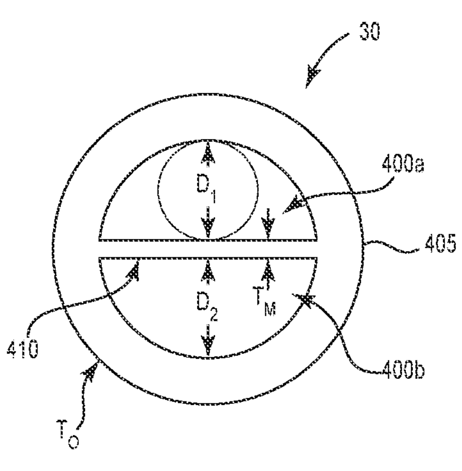
FIGS. 43 and 44 depict an embodiment of a catheter configured for use as a peripherally inserted dual lumen central catheter having an inlet lumen and an outlet lumen and for use with the system of FIG. 1.
Figure 44:
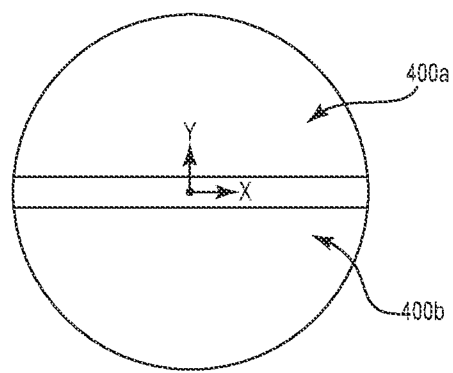

FIGS. 43 through 57 depict other embodiments of the catheter 30 having multiple lumens. FIGS. 43 and 44 depict a catheter 30 configured for use as a peripherally inserted central catheter (PICC) having an inlet lumen 400_a_ and an outlet lumen 400_b_. The inlet lumen 400_a_ has a surface area of about 0.00084 $in^2$ and a diameter $D_1$ of about 0.022 in. The outlet lumen 400_b_ has a surface area of 0.00084 $in^2$ and a diameter $D_2$ of about 0.022 in. The inlet and outlet lumens are defined by an outer wall 405 and a middle wall 410. The thickness $T_o$ of the outer wall 405 is about 0.010". The thickness $T_M$ of the middle wall 410 is about 0.004". Any other suitable material and dimensions also may be used.

Figures 45, 46:
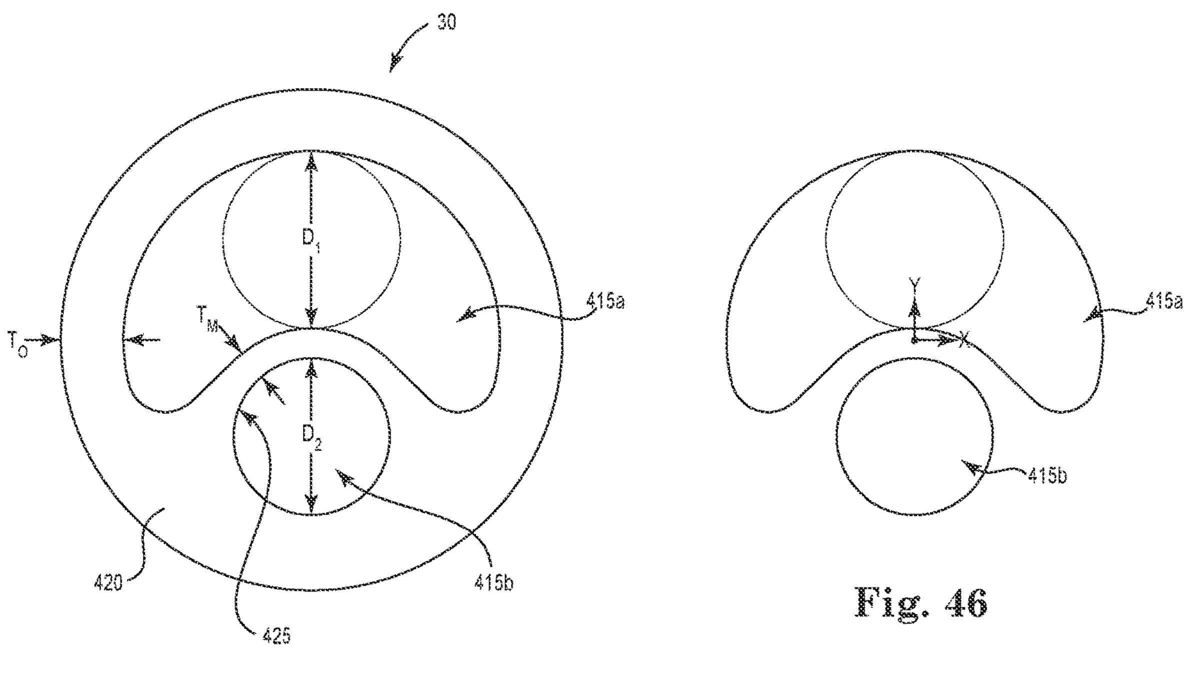
FIGS. 45 through 47 depict another embodiment of a dual lumen catheter for use with the system of FIG. 1.
Figure 47:
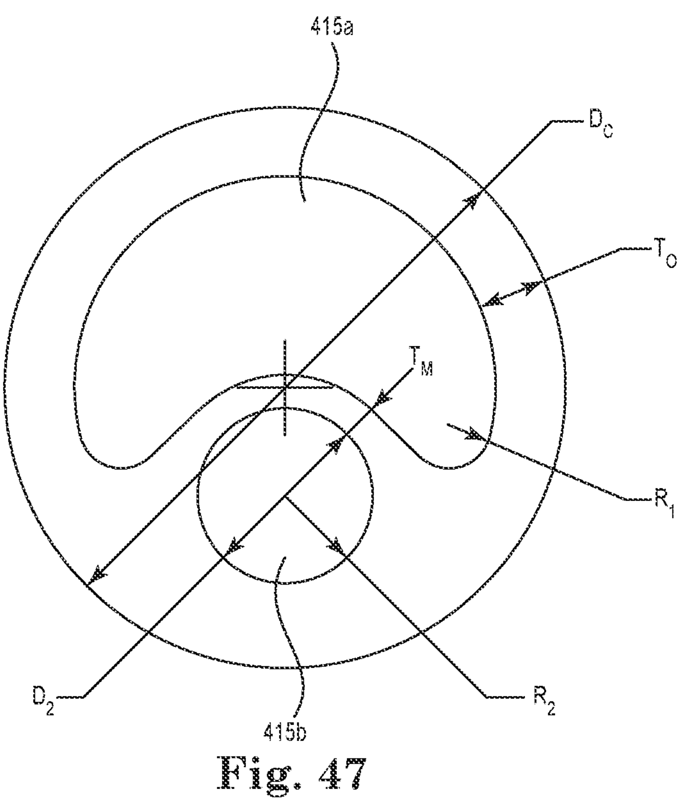

FIGS. 45 through 47 depict a dual lumen catheter 30 having an inlet lumen 415_a_ and an outlet lumen 415_b_. The inlet lumen 415_a_ has a surface area of about 0.00115 $in^2$ and a diameter $D_1$ of about 0.023". The outlet lumen 415_b_ has a surface area of about 0.000314 $in.^2$ and a diameter $D_2$ of about 0.020 in. The inlet and outlet lumens are defined by an outer wall 420 and a middle wall 425. The thickness $T_o$ of the outer wall 420 is about 0.008". The thickness $T_M$ of the middle wall 425 is about 0.004". The radius of curvature $R_1$ of the inlet lumen 415_a_ is about 0.005". The radius $R_2$ of the outlet lumen is about 0.014". The diameter $D_C$ of the catheter 30 is about 0.065". Any other suitable material and dimensions also may be used.

Figures 48, 49:
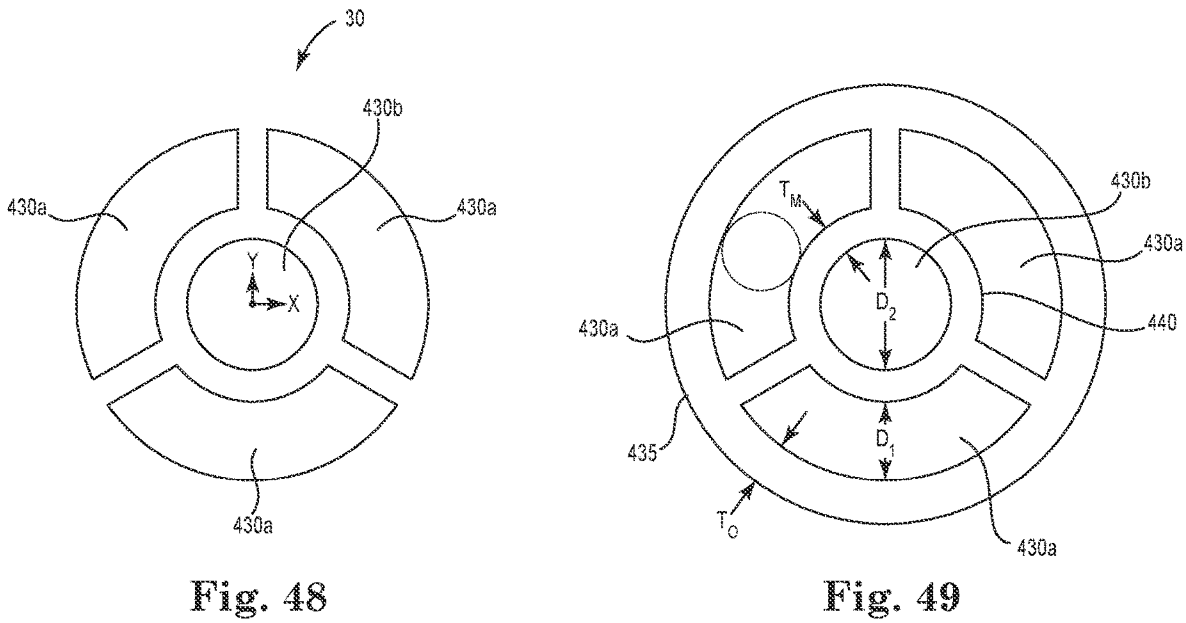
FIGS. 48 through 50 depict an embodiment of a multi-lumen catheter for use with the system of FIG. 1 having three inlet lumens and an outlet lumen.
Figure 50:
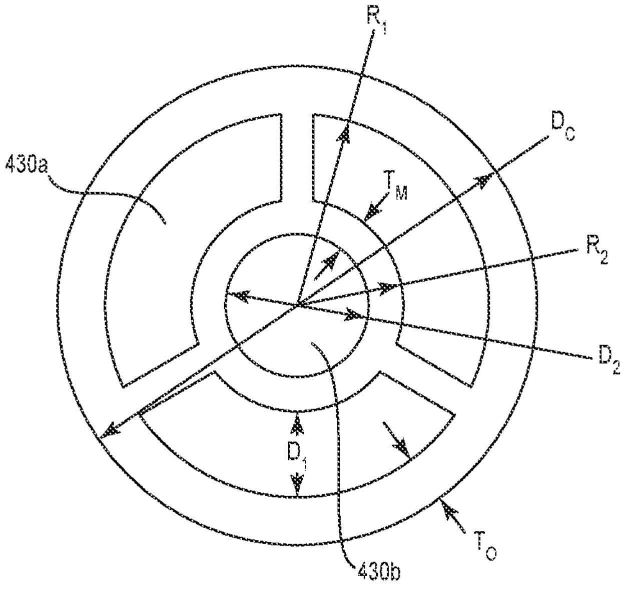

FIGS. 48 through 50 depict a multi-lumen catheter 30 having three inlet lumens 430_a_ and an outlet lumen 430_b_. Other embodiments may include a greater number of inlet or outlet lumens. The inlet lumens 430_a_ have a total surface area of about 0.00144 $in^2$ and each has a diameter $D_1$ of about 0.012 in. The outlet lumen 430_b_ has a surface area of about 0.00031 $in^2$ and a diameter $D_2$ of about 0.020 in. The inlet and outlet lumens are defined by an outer wall 435 and a middle wall 440. The thickness $T_o$ of the outer wall 435 is about 0.006". The thickness $T_M$ of the middle wall 440 is about 0.004". The radius $R_1$ of the inlet lumen 430_a_ is about 0.013". The radius $R_2$ of the outlet lumen 430_b_ is about 0.027". The diameter $D_C$ of the catheter 30 is about 0.065". Any other suitable material and dimensions also may be used.

Figures 51, 52:
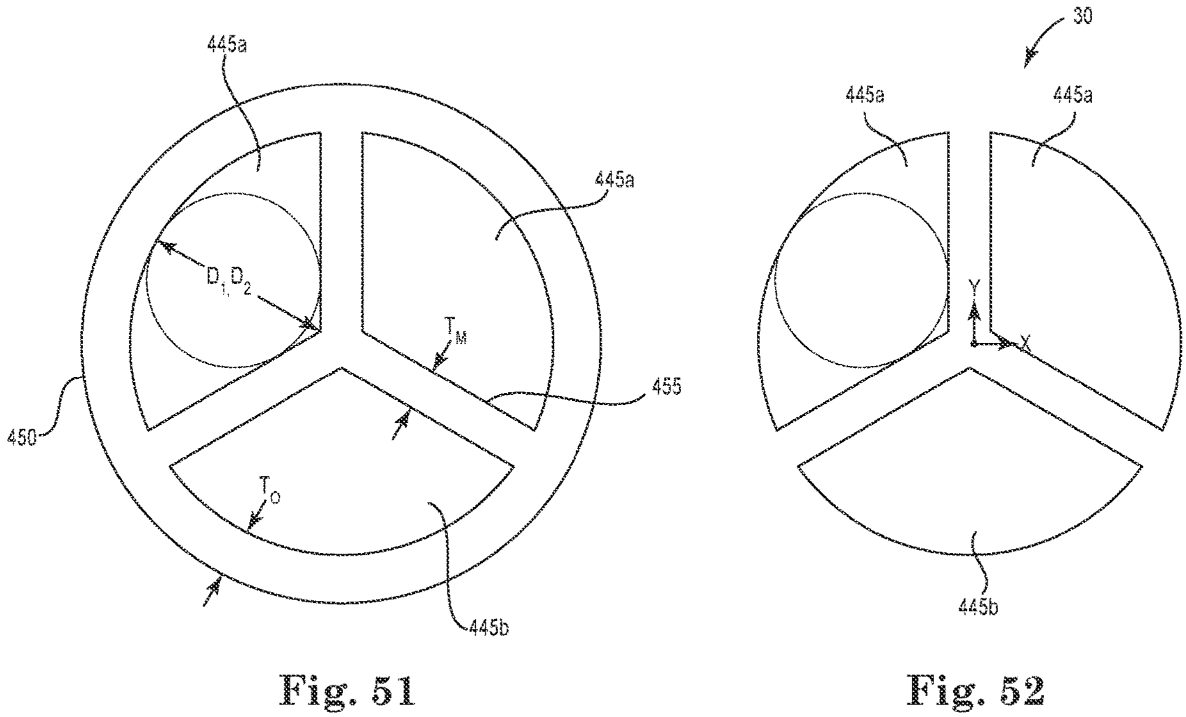
FIGS. 51 through 53 depict an embodiment of a multi-lumen catheter for use with the system of FIG. 1 having two inlet lumens and an outlet lumen.
Figure 53:
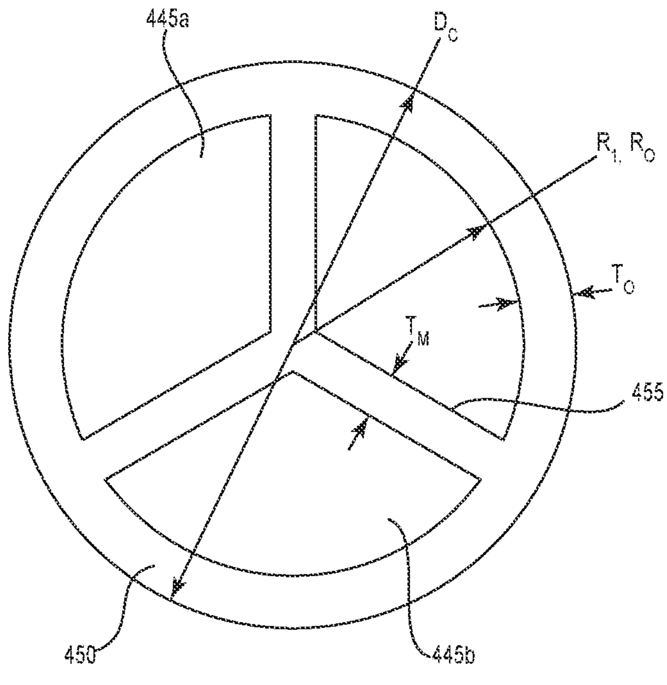
Figures 54, 55:
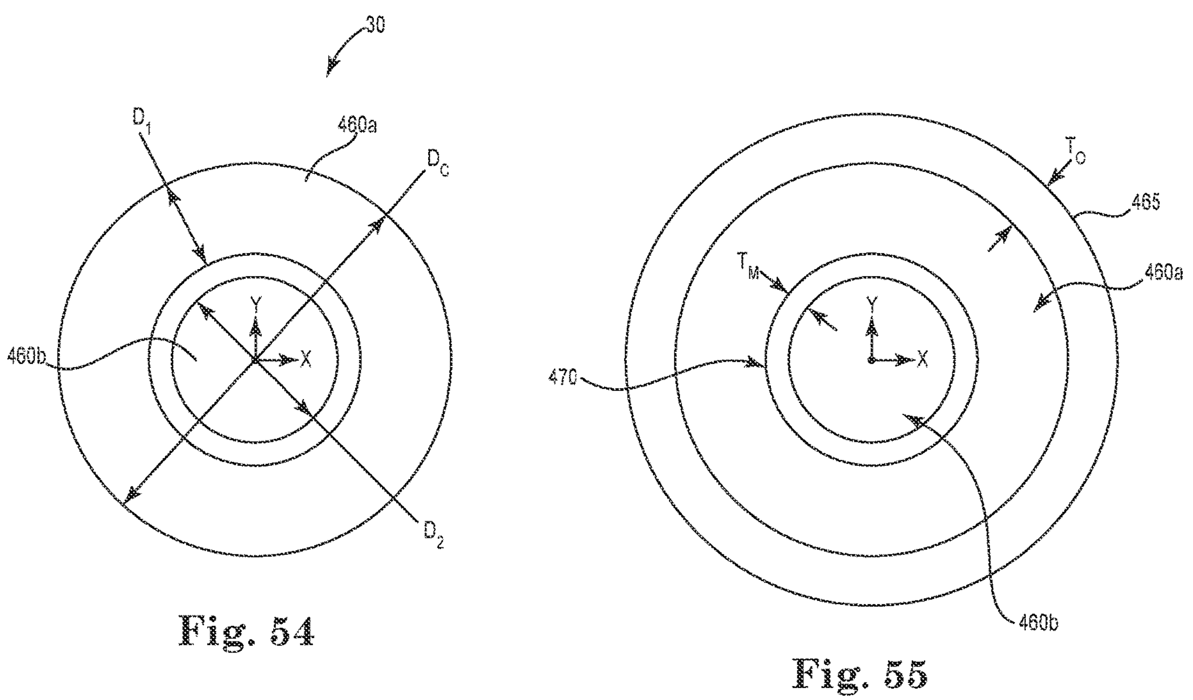
FIGS. 54 and 55 depict another embodiment of a dual lumen catheter for use with the system of FIG. 1.

FIGS. 51 through 53 depict a multi-lumen catheter 30 having two inlet lumens 445_a_ and an outlet lumen 445_b_. Other embodiments may include a greater number of inlet or outlet lumens or the inlet and outlet lumens may be positioned differently relative to each other. The inlet lumens 445_a_ have a total surface area of about 0.0013 $in^2$ and each has a diameter $D_1$ of about 0.022". The outlet lumen 445_b_ has a surface area of about 0.00065" $in^2$ and a diameter $D_2$ of about 0.022". The inlet and outlet lumens are defined by an outer wall 450 and a middle wall 455. The thickness $T_o$ of the outer wall 450 is about 0.006". The thickness $T_M$ of the middle wall 455 is about 0.004". The radius $R_1$ of the inlet lumen 445_a_ is about 0.027". The radius $R_2$ of the outlet lumen 445_b_ is about 0.027". The diameter $D_C$ of the catheter 30 is about 0.065". Any other suitable material and dimensions also may be used.

Figures 56, 57:
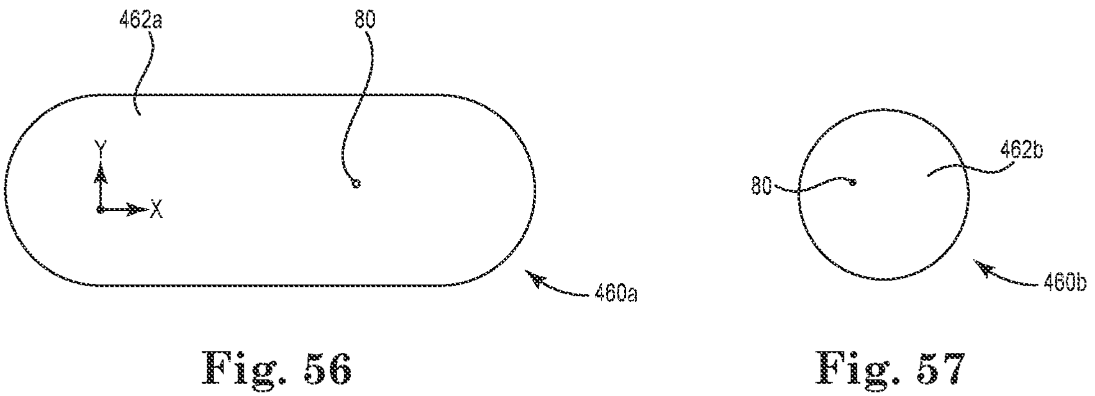
FIGS. 56 and 57 illustrate openings of an inlet lumen and an outlet lumen, respectively.

FIGS. 54 through 57 depict a dual lumen catheter 30 having an inlet lumen 460_a_ and an outlet lumen 460_b_. The inlet lumen 460_a_ has a surface area of about 0.00151 $in^2$ and a diameter $D_1$ of about 0.044". The outlet lumen 460_b_ has a surface area of about 0.00038 $in^2$ and a diameter $D_2$ of about 0.022". The inlet and outlet lumens are defined by an outer wall 465 and a middle wall 470. The thickness $T_o$ of the outer wall 465 is about 0.0065". The thickness $T_M$ of the middle or inner wall 470 is about 0.003". The diameter $D_C$ of the catheter 30 is about 0.065". As shown in FIGS. 56 and 57, and discussed in more detail above, the inlet lumen 460_a_ and outlet lumen 460_b_ may optionally include one or more openings 80 along certain portions of the catheter to increase the CSF or other fluid flow through the system 5. FIGS. 56 and 57 illustrate one opening 80 in each of the inlet and outlet lumens for clarity but it is understood that each lumen may include one or more openings 80. The openings 80 may be elongated openings defined within the outer circumferential wall 462_a_ of the inlet lumen 460_a_ and/or in the outer circumferential wall 462_b_ of the outlet lumen 460_b_. The openings 80 may be of oval, elliptical, other, or undefined shape. In some embodiments, the one or more openings 80 defined in the outer circumferential wall 462_a_ of the inlet lumen 460_a_ has a total cross sectional surface area of approximately 0.00126 $in^2$ and the size of each individual opening 80 is approximately 0.022"×0.062". The one or more openings 80 defined in the outer circumferential wall 462_b_ of the outlet lumen 460_b_ has a total cross sectional surface area of approximately 0.000314 $in^2$ and the diameter of each individual opening 80 is approximately 0.020 in. Any other suitable material and dimensions also may be used.

FIGS. 58 and 59 are surface area comparison charts. FIG. 58 shows a comparison of the distal/outlet lumens of the catheters of the present disclosure in comparison to the surface area of the distal/outlet lumens of known catheters. FIG. 59 shows a comparison of the proximal/inlet lumens of the catheters of the present disclosure in comparison to the surface area of the proximal/inlet lumens of known catheters.

FIGS. 60-66, 67-71, and 72-75 illustrate overall views, proximal subassembly views, and distal subassembly views, respectively, of an embodiment of a catheter 500 according to certain implementations. FIG. 60 illustrates a Y-connector portion 502, a proximal subassembly 540, and a distal subassembly 560. The Y-connector portion 502 may include connectors 504, 506, features 508, 510, 512, position marker 514, and other components. The connectors 504, 506 may take various forms. For example, as illustrated, the connectors 504, 506 are female and male Luer-lock connectors, respectively. The features 508, 510, 512 may be strain relief and kink resistance features, for example, as described above with reference to strain relief and kink resistance feature 60. The feature 508 may be configured to allow flex or deformation of the catheter 500 at portions near a central meeting point of the Y-connector 502. The features 510, 512 may be configured to allow flex or deformation of the catheter 500 near the connectors 504, 506. In certain implementations, the features 510, 512 may be color coded to indicate to which lumen of a multi-lumen catheter, the connectors 504, 506, correspond. In certain embodiments, the features 508, 510, 512 may take the form of approximately ⅛" polyolefin heat shrink tubing. The position marker 514 may be a position marker as described above with reference to position marker 100.

The length $L_1$ of the catheter 500 may be approximately 1,300 mm with a working length $L_2$ of approximately 1,150 mm. The working length $L_2$ may be defined based on various use and design considerations. As illustrated, the working length $L_2$ is the distance from the distal end of the distal subassembly 560 to the distal end of the feature 508. The distance $D_1$ from the distal end of the feature 508 to the proximal end of the connector 506 may be approximately 150 mm. The feature 508 may have a length $L_3$ of approximately 35 mm and the features 510, 512 may have a length $L_4$ of approximately 7 mm. In certain implementations, the catheter 500 may have a length $L_1$ of between approximately 400 mm and approximately 1200 cm, with the working length $L_2$ and other measurements changed accordingly.

FIG. 61 illustrates a sectional view taken from the region of the catheter 500 marked with cutting plane line A-A. This view illustrates a lumen 516A defined by a wall 516B. The characteristics and properties of the lumen 516A and wall 516B may be similar to the other walls and lumens described herein. As illustrated, the wall 516B has an inner diameter $D_2$ of approximately 0.54 mm and an outer diameter $D_3$ of approximately 1.14 mm.

FIG. 62 illustrates a sectional view taken from the region of the catheter 500 marked with cutting plane line B-B. This view illustrates a lumen 518A defined by an inner wall 518B and a lumen 520A defined by the space between the inner wall 518B and an outer wall 520B. The characteristics and properties of the lumens 518A, 520A and the walls 518B, 520B may be similar to the other walls and lumens described herein. The inner wall 518B may have an inner diameter $D_4$ of approximately 0.56 mm and an outer diameter $D_5$ of approximately 0.71 mm. The outer wall 520B may have an inner diameter of approximately 1.32 mm and an outer diameter of approximately 1.689 mm.

FIG. 63 illustrates an enlarged, detail view of a portion of the Y-connector 502 according to certain implementations, including tubes 522, first branch 524, and second branch 526. The tubes 522 may be hypotubes or other lengths of tubing. The tubes 522 may have a length $L_5$ of approximately 10 mm. In certain implementations, the first branch 524 may place the connector 504 in fluid connection with the lumen 520A and the second branch 526 may place the connector 506 in fluid connection with the lumen 518A.

Figure 64:
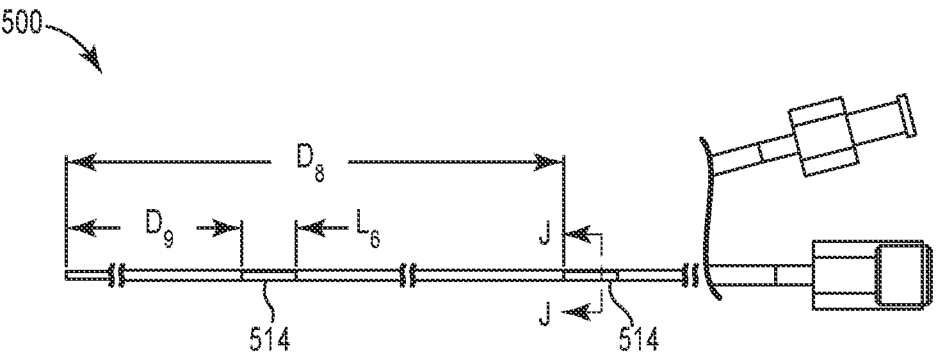
FIG. 64 illustrates the location of position markers on a catheter according to certain implementations.

FIG. 64 illustrates the location of two position markers 514 on the catheter 500. The distal end of the first position marker 514 is located a distance $D_9$ of approximately 450 mm away from the distal end of the catheter 500. The distal end of the second position marker 514 is located a distance $D_8$ of approximately 550 mm away from the distal end of the catheter 500. The length $L_4$ of the position markers 514 is approximately 10 mm. In certain implementations, the bands and/or position markers (such as position markers 514) may comprise PET heat shrink tubing.

Figure 65:
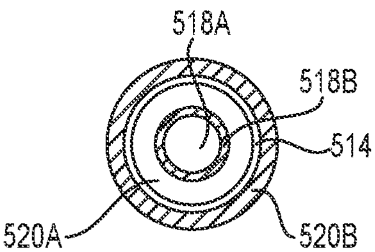
FIG. 65 illustrates a sectional view taken from the region of the catheter of FIG. 64 marked with the cutting plane line J-J.

FIG. 65 illustrates a sectional view taken from the region of the catheter 500 marked with the cutting plane line J-J. This view illustrates an embodiment wherein an outer portion of the position marker 514 is substantially adjacent to an inner portion of the wall 520B. Accordingly, in this portion of this embodiment, the lumen 520A is defined by the outer portion of the wall 518B and the inner portion of the position marker 514. As illustrated, the outer wall 520B has an outer diameter $D_{10}$ of approximately 1.75 mm.

Figure 66:
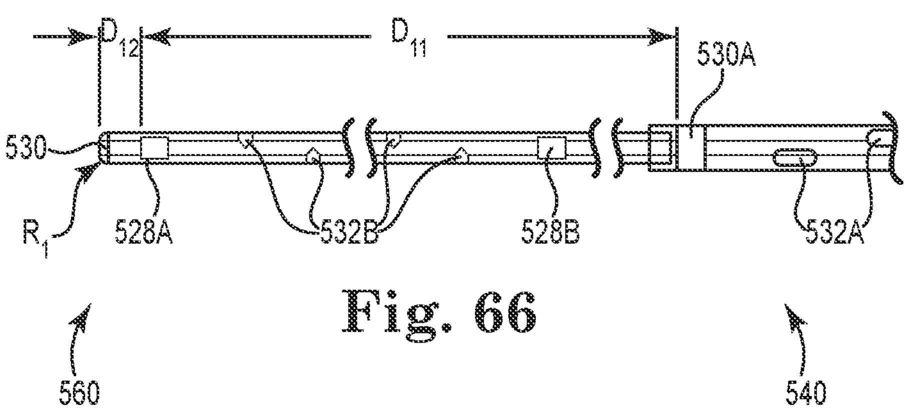
FIG. 66 illustrates a portion of a catheter near the joining of a proximal subassembly and a distal subassembly according to certain implementations.

FIG. 66 illustrates a portion of the catheter 500 near the joining of the proximal subassembly 540 and the distal subassembly 560, including bands 528A, 528B, 530, openings 532, and a radiused tip 534. The distal portion of the band 530A may be located a distance $D_{11}$ of approximately 300 mm away from the distal portion of the band 528A. The distal end of the band 528A may be located a distance $D_{12}$ of approximately 2 mm away from the distal end of the radiused tip 530. The radiused tip may have a radius $R_1$ of approximately 0.28 mm.

FIG. 67 illustrates a portion of the proximal subassembly 540. As illustrated, the distance $D_1$ from the distal end of the proximal subassembly 540 to the proximal end of the proximal subassembly 540 is approximately 893 mm. The distance $D_2$ from a distal end of a marker band 544B to a distal end of a band 530A is approximately 248 mm. A distance $D_4$ from a proximal end of the proximal subassembly 540 to the distal end of a band 530B is approximately 845 mm. A distance $D_3$ from a distal end of the marker band 544A to a distal end of the band 530A is approximately 148 mm. The marker bands 544A, 544B may have a length $L_1$ of approximately 10 mm. A portion of the proximal subassembly 540 may comprise coiled wire 542A having a coil pitch of approximately 0.018". A portion of the proximal subassembly 540 may comprise coiled wire 542B having a coil pitch of approximately 0.095". In certain implementations, the wires 542A, 542B may comprise approximately 0.003" round wire spool of 304V spring temper material.

In certain implementations, the proximal subassembly 540 of the catheter 500 may have an outer diameter of between approximately 0.06" and approximately 0.07". This configuration may maximize the size of the catheter between layers of tissue to enable a desired level of drainage and/or suction without collapse. The thickness of the proximal subassembly 540 and other sections of the catheter 500 may be a function of a design of one or more layers of coil and sheath. The thickness may affect the stiffness and pushability of the catheter 500 and kink-resistance. In certain implementations, the diameter of an inner lumen of the catheter 500 (such as the diameter of a lumen of the proximal subassembly 540) may be chosen to provide optimum drainage and/or suction given the constraints of particular anatomy or procedures. For example, the minimum diameter of a proximal inner lumen may be chosen to be between approximately 0.025" and approximately 0.060".

FIG. 68 illustrates a detail view of the proximal subassembly 540 of FIG. 67. As illustrated, a portion of the proximal subassembly 540 defines a plurality of openings 532A. The openings 532A may be in fluid connection with a lumen of the catheter 500. The openings 532A may be spaced with 2 coil pitch spacing of the wire 542A. The distance $D_6$ between the distal end of the band 530B and the distal end of the band 530A is approximately 45 mm. A distance $D_5$ from the distal end of the band 530A to the distal end of the proximal subassembly 540 may be approximately 3 mm. In certain implementations, the bands 530A, 530B may comprise a PT/10% IR band having an inner diameter of approximately 0.061" and an outer diameter of approximately 0.064".

FIG. 69 illustrates a sectional view taken from the region of the proximal subassembly 540 marked with the cutting plane line A-A, including a liner 546 and tubing 548. The liner 546 and the tubing 548 may be arranged such that the tubing 548 is within the liner 546. In certain implementations, the liner 456 may comprise approximately 0.001" WT PTFE liner. The tubing 548 may comprise approximately 0.004" WT polyether block amide tubing. The outer diameter $D_7$ of the combination tubing 548 and liner 546 may be approximately 1.69 mm. The inner diameter $D_8$ of the same may be approximately 1.32 mm.

FIG. 70 illustrates a detail view of a portion of the proximal subassembly 540 taken from the view of line D-D and illustrating one of the openings 532A. The illustrated opening 532A has dimensions of approximately 1.57 mm by approximately 0.56 mm.

FIG. 71 illustrates a sectional view taken from the region of the proximal subassembly 540 marked with the cutting plane E-E. As illustrated the outer diameter $D_9$ this portion, inclusive of marker band 544 is approximately 1.75 mm.

FIG. 72 illustrates a portion of the distal subassembly 560. The length $L_1$ of the distal subassembly 560 may be approximately 302 mm. The distance $D_1$ from the proximal end of the distal subassembly 560 to the distal end of a band 528B is approximately 270 mm. A portion of the distal subassembly 560 may comprise a coiled wire 462B may have a coil pitch of approximately 0.032". This and other portions of the catheter 500 may comprise approximately 0.003" WT nylon 12 tubing having an inner diameter of approximately 0.022"

and approximately 0.007" WT PEBAX tubing having an inner diameter of approximately 0.04".

FIG. 73 illustrates a detailed portion of the distal subassembly 560, including the band 528A, a plurality of openings 532B, the band 528B, a wire 462A, and the wire 462B. In certain implementations, the wires 462A, 462B may be different portions of the same wire or may be separate sections of wire. As illustrated, the wire 462A and 462B may be separated by band 528B. The wire 462A may have a coil pitch of approximately 0.065". The wires 462A, 462B may comprise approximately 0.003" round wire spool 304V spring temper material. The openings 532B may be spaced with 2 coil pitch spacing and arranged on a top and a bottom portion of the catheter 500 and made a fluid connection with an inner lumen of the catheter 500. A distance $D_2$ between the distal end of the band 528B and the distal end of the band 528A may be approximately 30 mm. The wire 462A may be disposed within this region. The bands 528A, 528B may have an inner diameter of approximately 0.032" and an outer diameter of approximately 0.034". The bands 528A, 528B may comprise a material of PT/10% IR.

FIG. 74 illustrates a detailed portion of the distal subassembly 560, including the radiused tip 530, the band 528A, and the wire 462A. The distance from the distal end of the band 528A and the distal end of the radiused tip 530 is approximately 2 mm. The radiused tip may have a radius $R_1$ of approximately 0.28 mm.

FIG. 75 illustrates a sectional view taken from the region of the distal subassembly 560 marked with the cutting plane A-A. As illustrated, this section of the distal subassembly 560 has an outer diameter of approximately 1.14 mm and an inner diameter of approximately 0.53 mm.

All directional references (e.g., proximal, distal, upper, lower, upward, downward, left, right, lateral, front, back, top, bottom, above, below, vertical, horizontal, clockwise, and counterclockwise) are only used for identification purposes to aid the reader's understanding of the present invention, and do not create limitations, particularly as to the position, orientation, or use of the invention. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other. It should be noted that delivery sheath and delivery catheter may be used interchangeably for purposes of this description. The exemplary drawings are for purposes of illustration only and the dimensions, positions, order and relative sizes reflected in the drawings attached hereto may vary.

The above specification, examples and data provide a complete description of the structure and use of exemplary embodiments of the invention as claimed below. Although various embodiments of the invention as claimed have been described above with a certain degree of particularity, or with reference to one or more individual embodiments, those skilled in the art could make numerous alterations to the disclosed embodiments without departing from the spirit or scope of this invention. Other embodiments are therefore contemplated. It is intended that all matter contained in the above description and shown in the accompanying drawings shall be interpreted as illustrative only of particular embodiments and not limiting. Changes in detail or structure may be made without departing from the basic elements of the invention as defined in the following claims.

What is claimed is:

1. A catheter comprising:

a proximal subassembly defining two proximal lumens, a proximal subassembly coil having a first pitch, and a plurality of first openings each extending through a wall of the proximal subassembly and disposed between adjacent coil windings of the proximal subassembly coil;

a distal subassembly defining a single distal lumen, a distal subassembly coil having a second pitch which is larger than the first pitch, and a plurality of second openings each extending through a wall of the distal subassembly and disposed between adjacent coil windings of the distal subassembly coil, wherein the plurality of second openings are arranged only in an alternating fashion on a top and a bottom portion of the catheter and each have a two coil pitch spacing;

wherein the proximal subassembly coil and the distal subassembly coil are separate and discontinuous with one another; and wherein the distal subassembly coil is embedded in the wall of the distal subassembly.

2. The catheter of claim 1, wherein the proximal subassembly includes an inner wall and an outer wall.

3. The catheter of claim 2, wherein the two proximal lumens include a first lumen and a second lumen, and the first lumen is defined by the inner wall, and the second lumen is defined by a space between the inner wall and the outer wall.

4. The catheter of claim 3, wherein the plurality of first openings each extend through the outer wall of the proximal subassembly and are in fluid communication with the second lumen.

5. The catheter of claim 1, wherein the wall of the distal subassembly defines the single distal lumen.

6. The catheter of claim 2, wherein the distal subassembly includes a first outer diameter and the proximal subassembly includes a second outer diameter that is larger than the first outer diameter.

7. The catheter of claim 1, wherein the proximal subassembly coil includes a distal coiled portion having the first pitch, and a proximal coiled portion having a third pitch smaller than the first pitch.

8. The catheter of claim 1, wherein the distal subassembly coil includes a distal coiled portion having the second pitch, and a proximal coiled portion having a fourth pitch smaller than the second pitch.

9. The catheter of claim 1, wherein the plurality of first openings are spaced with a two coil pitch spacing of the proximal subassembly coil.

10. A catheter comprising:

a proximal subassembly defining two proximal lumens, a proximal subassembly coil having a first pitch, and a plurality of first openings each extending through a wall of the proximal subassembly and disposed between adjacent coil windings of the proximal subassembly coil;

a distal subassembly defining a single distal lumen, a distal subassembly coil having a second pitch which is larger than the first pitch, and a plurality of second openings each extending through a wall of the distal subassembly and disposed between adjacent coil windings of the distal subassembly coil, wherein the plurality of second openings are arranged only in an alternating fashion on a top and a bottom portion of the catheter and each have a two coil pitch spacing; wherein the proximal subassembly coil is formed from a first wire; wherein the distal subassembly coil is formed from a second wire different from the first wire; wherein the distal subassembly coil is embedded in the wall of the distal subassembly, and wherein the first pitch is in a range from approximately 0.01 inches to approximately 0.03 inches.

11. The catheter of claim 10, wherein the plurality of first openings have a two coil pitch spacing of the proximal subassembly coil.

12. A catheter comprising:

a proximal subassembly defining two proximal lumens, a proximal subassembly coil having a first pitch, and a plurality of first openings each extending through a wall of the proximal subassembly and disposed between adjacent coil windings of the proximal subassembly coil;

a distal subassembly defining a single distal lumen, a distal subassembly coil having a second pitch which is larger than the first pitch, and a plurality of second openings each extending through a wall of the distal subassembly and disposed between adjacent coil windings of the distal subassembly coil, wherein the plurality of second openings are arranged only in an alternating fashion on a top and a bottom portion of the catheter and each have a constant spacing;

wherein the proximal subassembly coil and the distal subassembly coil are separated from one another;

wherein the first pitch is in a range from approximately 0.01 inches to approximately 0.03 inches;

wherein the second pitch is in a range from approximately 0.06 inches to approximately 0.07 inches; and wherein the distal subassembly coil is embedded in the wall of the distal subassembly.

13. The catheter of claim 12, wherein the plurality of first openings have a two coil pitch spacing of the proximal subassembly coil.

* * * * *